US011707247B2

(12) United States Patent
Xiao et al.

(10) Patent No.: US 11,707,247 B2
(45) Date of Patent: *Jul. 25, 2023

(54) SYSTEMS AND METHODS FOR CONTROLLING AN X-RAY IMAGING DEVICE

(71) Applicant: SHANGHAI UNITED IMAGING HEALTHCARE CO., LTD., Shanghai (CN)

(72) Inventors: Yongqin Xiao, Shanghai (CN); Shouyuan Jin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 109 days.

This patent is subject to a terminal disclaimer.

(21) Appl. No.: 17/180,921

(22) Filed: Feb. 22, 2021

(65) Prior Publication Data
US 2021/0212652 A1 Jul. 15, 2021

Related U.S. Application Data

(63) Continuation of application No. 16/023,028, filed on Jun. 29, 2018, now Pat. No. 10,925,570, which is a (Continued)

(30) Foreign Application Priority Data

Apr. 28, 2017 (CN) .......................... 201710298474.2
May 31, 2017 (CN) .......................... 201710399426.2
(Continued)

(51) Int. Cl.
*A61B 6/00* (2006.01)
*G01N 23/04* (2018.01)

(52) U.S. Cl.
CPC .............. *A61B 6/542* (2013.01); *A61B 6/465* (2013.01); *A61B 6/54* (2013.01); *A61B 6/4405* (2013.01); *G01N 23/04* (2013.01)

(58) Field of Classification Search
CPC ........... A61B 6/00; A61B 6/542; A61B 6/465; A61B 6/54; A61B 6/46; A61B 6/464;
(Continued)

(56) References Cited

U.S. PATENT DOCUMENTS 5,206,894 A    4/1993  Makrinos et al.
9,788,809 B2  10/2017  Hiroike et al.
(Continued)

FOREIGN PATENT DOCUMENTS

CN        2751349 Y       1/2006
CN     102280061 A       12/2011
(Continued)

OTHER PUBLICATIONS

International Search Report in PCT/CN2017/105052 dated Jan. 26, 2018, 5 pages.
(Continued)

Primary Examiner — Jurie Yun
(74) Attorney, Agent, or Firm — Metis IP LLC

(57) ABSTRACT

A system includes one or more storage devices storing a set of instructions and at least one processor in communication with the storage device. When executing the instructions, the at least one processor is configured to cause the system to obtain a first operating state of an X-ray imaging device, and obtain a first input from a user via a terminal, the first input being associated with a second operating state of the X-ray imaging device. The at least one processor may further cause the system to determine whether the first input satisfies a switch condition. Upon a determination that the first input satisfies the switch condition, the at least one processor may (Continued)

further cause the system to transmit a first instruction to switch the X-ray imaging device from the first operating state to the second operating state.

20 Claims, 18 Drawing Sheets

Related U.S. Application Data continuation of application No. PCT/CN2017/105052, filed on Sep. 30, 2017.

(30) Foreign Application Priority Data

May 31, 2017 (CN) .......................... 201710401354.0
May 31, 2017 (CN) .......................... 201720622821.8

(58) Field of Classification Search
CPC ........ A61B 6/4405; G01N 23/04; H05G 1/58; H05G 1/56
See application file for complete search history.

(56) References Cited

U.S. PATENT DOCUMENTS

| | | | |
|---|---|---|---|
| 10,368,826 B2 | 8/2019 | Tamura | |
| 10,638,999 B2 | 5/2020 | Shah | |
| 10,925,570 B2 * | 2/2021 | Xiao | ........................ A61B 6/54 |
| 2006/0173270 A1 | 8/2006 | Weiner | |
| 2010/0177218 A1 | 7/2010 | Ohuchi | |
| 2011/0288853 A1 | 11/2011 | Butzine et al. | |
| 2012/0300906 A1 | 11/2012 | Matsumoto | |
| 2014/0241510 A1 | 8/2014 | Wang | |
| 2014/0254760 A1 | 9/2014 | Hiroike | |
| 2014/0276056 A1 | 9/2014 | Ohta et al. | |
| 2015/0235354 A1 | 8/2015 | Rongen et al. | |
| 2015/0281564 A1 | 10/2015 | Shin | |
| 2018/0153499 A1 | 6/2018 | Tobita et al. | |

FOREIGN PATENT DOCUMENTS

| | | |
|---|---|---|
| CN | 102495768 A | 6/2012 |
| CN | 103001625 A | 3/2013 |
| CN | 103116450 A | 5/2013 |
| CN | 103202700 A | 7/2013 |
| CN | 103268184 A | 8/2013 |
| CN | 204016316 U | 12/2014 |
| CN | 204950979 U | 1/2016 |
| CN | 204965069 U | 1/2016 |
| CN | 107137100 A | 9/2017 |
| CN | 107157500 A | 9/2017 |
| CN | 107157501 A | 9/2017 |
| CN | 207041530 U | 2/2018 |

OTHER PUBLICATIONS

Written Opinion in PCT/CN2017/105052 dated Jan. 26, 2018, 5 pages.
First Office Action in Chinese Application No. 201710298474.2 dated May 8, 2019, 20 pages.
The Extended European Search Report in European Application No. 17906808.5 dated Mar. 19, 2020, 6 pages.
The Third Office Action in Chinese Application No. 201710298474.2 dated Mar. 1, 2021, 17 pages.
First Office Action in Chinese Application No. 201780090139.1 dated Aug. 18, 2022, 21 pages.

* cited by examiner

1200

1200

1300

SYSTEMS AND METHODS FOR CONTROLLING AN X-RAY IMAGING DEVICE

CROSS-REFERENCE TO RELATED APPLICATIONS

This application is a Continuation of U.S. application Ser. No. 16/023,028, filed on Jun. 29, 2018, which is a Continuation of International Application No. PCT/CN2017/105052, filed on Sep. 30, 2017, which claims priority to Chinese Patent Application No. 201710298474.2, filed on Apr. 28, 2017, Chinese Patent Application No. 201710401354.0, filed on May 31, 2017, Chinese Patent Application No. 201710399426.2, filed on May 31, 2017, and Chinese Patent Application No. 201720622821.8, filed on May 31, 2017. Each of the above-referenced applications is expressly incorporated herein by reference in their entireties.

TECHNICAL FIELD

The present disclosure generally relates to X-ray imaging, and more particularly, to systems and methods for controlling an X-ray imaging device via a terminal.

BACKGROUND

X-ray imaging has been widely used in clinical examinations and medical diagnoses in recent years. When using an X-ray imaging device to perform a scan, a user (e.g., a doctor, a technician) needs to control the X-ray imaging device. For example, the doctor may control the exposure time of the X-ray imaging device during the scan via a control device (e.g., an exposure switch) mounted on the X-ray imaging device, which may cause unnecessary radiation to the doctor. Therefore, it is desirable to provide systems and methods for controlling the X-ray imaging device.

SUMMARY

According to an aspect of the present disclosure, a system may include one or more storage devices storing a set of instructions for controlling an X-ray imaging device and at least one processor configured to communicate with the one or more storage devices. When executing the set of instructions, the at least one processor may cause the system to obtain a first operating state of the X-ray imaging device and obtain a first input from a user via a terminal, the first input being associated with a second operating state of the X-ray imaging device. The at least one processor may also cause the system to determine whether the first input satisfies a switch condition. Upon a determination that the first input satisfies the switch condition, the at least one processor may further cause the system to transmit a first instruction to the X-ray imaging device to switch the X-ray imaging device from the first operating state to the second operating state.

In some embodiments, the terminal may include a first key associated with the second operating state of the X-ray imaging device.

In some embodiments, the at least one processor may cause the system to determine whether the first input includes a first selection of the first key. A time length of the first key being selected may be equal to or longer than a first time threshold.

In some embodiments, the terminal may further include a second key. The at least one processor may also cause the system to determine whether the first input includes a second selection of the first key and a third selection of the second key.

In some embodiments, the terminal may further include a touchscreen, and at least one of the first key or the second key may be located on the touchscreen.

In some embodiments, at least one of the first key or the second key may be a physical key.

In some embodiments, the second operating state of the X-ray imaging device may be at least one of an exposure pending state, an exposure preparation state, or an exposure state.

In some embodiments, the second operating state of the X-ray imaging device may be the exposure state. The at least one processor may also cause the system to determine a first exposure time based on the first input.

In some embodiments, the second operating state of the X-ray imaging device may be the exposure preparation state. The at least one processor may also cause the system to obtain a second input via the terminal, the second input being associated with the exposure state of the X-ray imaging device. The at least one processor may further cause the system to determine a second exposure time of the X-ray imaging device based on the second input.

In some embodiments, the second operating state of the X-ray imaging device may be the exposure preparation state. The at least one processor may also cause the system to determine whether a third input is obtained within a second time threshold via the terminal, the third input being associated with the exposure state of the X-ray imaging device. Upon a determination that the third input is not obtained within the second time threshold via the terminal, the at least one processor may further cause the system to transmit a second instruction to the X-ray imaging device to switch the X-ray imaging device from the exposure preparation state to the exposure pending state.

In some embodiments, the terminal may include a first interface corresponding to the second operating state of the X-ray imaging device. The terminal may cause the system to determine whether the X-ray imaging device operates in the first operating state. In response to a result of the determination that the X-ray imaging device operates in the first operating state, the terminal display the first interface.

In some embodiments, the X-ray imaging device further includes a third operating state. The terminal may further include a second interface corresponding to the third operating state of the X-ray imaging device. Upon the determination that the first input satisfies the switch condition, the at least one processor may further cause the system to transmit a third instruction to the terminal to switch the terminal from the first interface to the second interface.

In some embodiments, the terminal may include an interface. The terminal may be configured to acquire image data captured by an image acquisition device mounted on the X-ray imaging device and display the image data on the interface.

According to another aspect of the present disclosure, a computer-implemented method may include one or more of the following operations performed by at least one processor. The method may include obtaining a first operating state of an X-ray imaging device. The method may also include obtaining a first operating state of an X-ray imaging device and obtaining a first input via a terminal, the first input being associated with a second operating state of the X-ray imaging device. The method may further include determining whether the first input satisfies a switch condition. Upon a determination that the first input satisfies the switch condition, the method may further include transmitting a first instruction to the X-ray imaging device to switch the X-ray imaging device from the first operating state to the second operating state.

According to yet another aspect of the present disclosure, a non-transitory computer-readable storage medium storing instructions that, when executed by at least one processor of a system, cause the system to perform a method. The method may include obtaining a first operating state of an X-ray imaging device. The method may also include obtaining a first operating state of an X-ray imaging device and obtaining a first input via a terminal, the first input being associated with a second operating state of the X-ray imaging device. The method may also include determining whether the first input satisfies a switch condition. Upon a determination that the first input satisfies the switch condition, the method may also include transmitting a first instruction to the X-ray imaging device to switch the X-ray imaging device from the first operating state to the second operating state.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
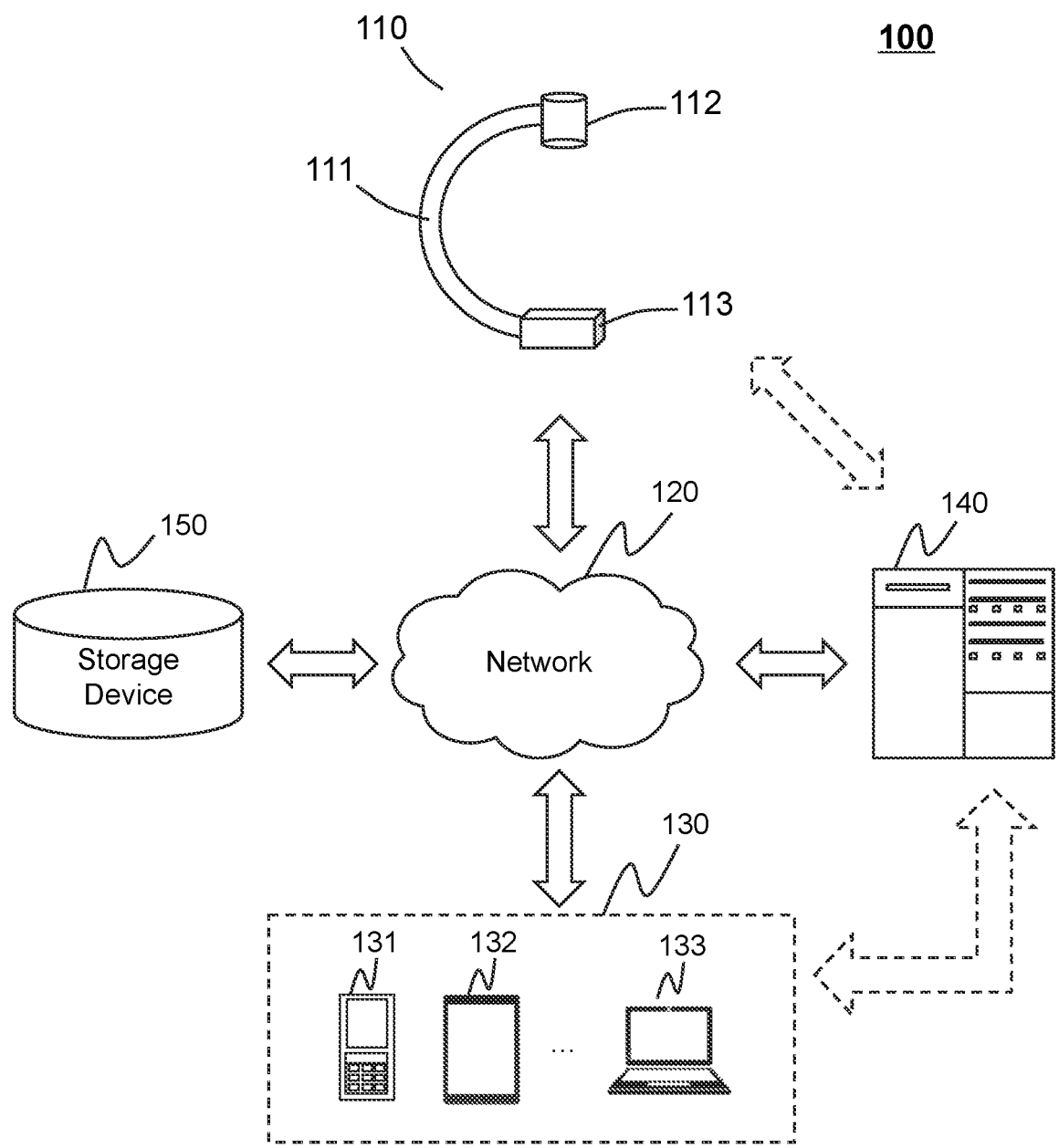
FIG. 1 is a schematic diagram illustrating an exemplary X-ray imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts.

Software modules/units/blocks configured for execution on computing devices (e.g., the processor 310 illustrated in FIG. 3 and/or the CPU 440 illustrated in FIG. 4) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging. In some embodiments, the imaging system may include a single modality imaging system and/or a multi-modality imaging system. The single modality imaging system may include, for example, an X-ray imaging system, an emission computed tomography (ECT) system, a magnetic resonance imaging (MRI) system, an ultrasonography system, a positron emission tomography (PET) system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, etc.

For illustration purposes, the disclosure describes systems and methods relating to X-ray imaging system. It should be noted that the X-ray imaging system described below is merely provided for illustration purposes, and not intended to limit the scope of the present disclosure.

An aspect of the present disclosure relates to systems and methods for controlling an X-ray imaging device via a terminal. The systems may perform the methods to obtain an operating state of the X-ray imaging device. The systems may perform the methods to obtain, from the terminal, an input associated with another operating state of the X-ray imaging device. The systems may perform the methods to determine whether the input received from the terminal satisfies a switch condition. Upon a determination that the input satisfies the switch condition, the systems may perform the methods to transmit an instruction to the X-ray imaging device to switch its operating state.

FIG. 1 is a schematic diagram illustrating an exemplary X-ray imaging system 100 according to some embodiments of the present disclosure. As shown in FIG. 1, the X-ray imaging system 100 may include an X-ray imaging device 110, a network 120, one or more terminals 130, a processing engine 140, and a storage device 150. The connection between the components in the X-ray imaging system 100 may be variable. For example, the X-ray imaging device 110 and/or the terminal(s) 130 may be connected to the processing engine 140 through the network 120. As another example, the X-ray imaging device 110 and/or the terminal(s) 130 may be connected to the processing engine 140 directly.

The X-ray imaging device 110 may be configured to scan an object using X-rays and generate imaging data used to generate one or more images relating to the object. In some embodiments, the X-ray imaging device 110 may transmit the imaging data to the processing engine 140 for further processing (e.g., generating one or more images). In some embodiments, the imaging data and/or the one or more images associated with the object may be stored in the storage device 150 and/or the processing engine 140.

In some embodiments, as shown in FIG. 1, the X-ray imaging device 110 may include a C-arm X-ray scanner. In some embodiments, the X-ray imaging device 110 may include a computed tomography (CT) scanner, a digital radiography (DR) scanner (e.g., a mobile digital radiography), a digital subtraction angiography (DSA) scanner, a dynamic spatial reconstruction (DSR) scanner, an X-ray microscopy scanner, a multimodality scanner, or the like, or a combination thereof. Exemplary multi-modality scanners may include a computed tomography-positron emission tomography (CT-PET) scanner, a computed tomography-magnetic resonance imaging (CT-MRI) scanner, etc. The object may be biological or non-biological. Merely by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

The X-ray imaging device 110 may include a support 111, an X-ray source 112, and a detector 113. The support 111 may be configured to support the X-ray source 112 and the detector 113. In some embodiments, the support 111 may have a C-shape as illustrated in FIG. 1. Alternatively, the support 111 may have a column-shape, an O-shape, a U-shape, a G-shape, or the like, or a combination thereof.

In some embodiments, the X-ray source 112 and the detector 113 may be connected to the support 111. For example, the support 111 may have a C-shape, a U-shape, a G-shape, etc. The support 111 may have a first end and a second end. The first end may be connected to the X-ray source 112, and the second end may be connected to the detector 113. As another example, the support 111 may have an O-shape. The X-ray source 112 and the detector 113 may be attached to the support 111 and spaced from each other. For instance, the detector 113 may be opposite to the X-ray source 112, and a line linking the detector 113 and the X-ray source 112 may pass through the center of the O-shape. In some embodiments, the detector 113 and the X-ray source 112 may be spaced apart by a space. The space may be configured to accommodate an object to be scanned.

In some embodiments, the X-ray source 112 and the detector 113 may move with the support 111. For example, the X-ray source 112 and the detector 113 may move with the support 111 using a movable device (e.g., a trolley, or wheels) mounted on the X-ray imaging device 110. In some embodiments, the X-ray source 112 and/or the detector 113 may be indirectly connected to the support 111. Merely by way of example, the X-ray imaging device 110 may include a robotic arm (not shown in FIG. 1). The robotic arm may include an end connected to the support 111. The robotic arm may also include and another end connected to the X-ray source 112. In some embodiments, the robotic arm may be movable and/or retractable.

The X-ray source 112 may emit one or more X-rays to the object. In some embodiments, the X-ray source 112 may include a tube, such as a cold cathode ion tube, a high vacuum hot cathode tube, a rotating anode tube, etc. The tube may be powered by a high voltage generator, emitting X-rays that may be detected by the detector 113. The X-rays emitted by the X-ray source 112 may be guided to form a beam having the shape of a line, a narrow pencil, a narrow fan, a fan, a cone, a wedge, an irregular shape, or the like, or a combination thereof.

The detector 113 may detect radioactive rays emitted from the X-ray source 112. In some embodiments, the detector 113 may be configured to produce an analog electrical signal that represents the intensity of the received X-rays, including the attenuated beam, as it passes through the object. In some embodiments, the detector 113 may include one or more detector units. The detector units may include a scintillation detector (e.g., a cesium iodide detector), a gas detector, etc. The pixels of the detector may be represented by the number of the smallest detector units, e.g., the number of detector units. The detector units of the detector 113 may be arranged in a single row, two rows, or another number of rows. The X-ray detector may be one-dimensional, two-dimensional, or three-dimensional.

In some embodiments, the X-ray imaging device 110 may operate in one or more operating states. Exemplary operating states of the X-ray imaging device 110 may include an exposure pending state, an exposure preparation state, an exposure state, a movable state, a fixed state, or the like, or any combination thereof. Details regarding the operating states of the X-ray imaging device 110 may be found elsewhere in the present disclosure (e.g., FIG. 6 and the relevant descriptions thereof).

The network 120 may include any suitable network that can facilitate the exchange of information and/or data for the X-ray imaging system 100. In some embodiments, one or more components of the X-ray imaging system 100 (e.g., the X-ray imaging device 110, the terminal(s) 130, the processing engine 140, the storage device 150, etc.) may communicate information and/or data with one or more other components of the X-ray imaging system 100 via the network 120. For example, the processing engine 140 may obtain image data from the X-ray imaging device 110 via the network 120. As another example, the processing engine 140 may obtain user instructions from the terminal(s) 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the X-ray imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, a virtual reality device, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a HoloLens™, a Gear VR™, etc. In some embodiments, the terminal(s) 130 may be part of the processing engine 140.

In some embodiments, the terminal 130 may control the operation of one or more components of the X-ray imaging system 100, such as the X-ray imaging device 110. For example, a user may set the operating state and/or operating parameters of the X-ray imaging device 110 via the terminal 130. In some embodiments, the terminal 130 may be integrated into the X-ray imaging device 110. For example, the terminal 130 may be a control panel mounted on the X-ray imaging device 110 configured to perform the functions of the terminal 130 disclosed in this application.

Figure 3:
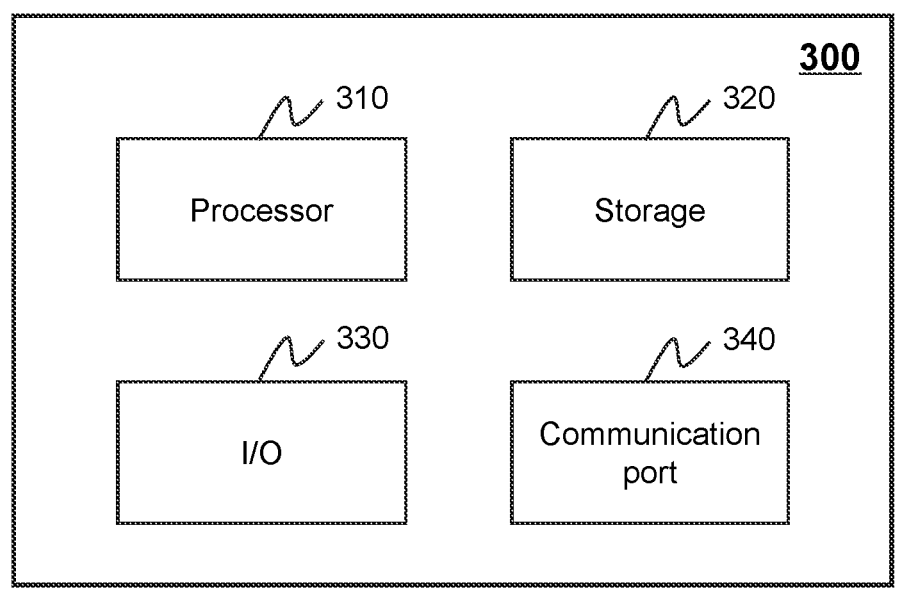
FIG. 3 is a schematic diagram illustrating exemplary hardware and/or software components of an exemplary computing device on which a processing engine may be implemented according to some embodiments of the present disclosure.

The processing engine 140 may process data and/or information obtained from the X-ray imaging device 110, the terminal(s) 130, and/or the storage device 150. For example, the processing engine 140 may process imaging data generated by the X-ray imaging device 110 to generate an image. As another example, the processing engine 140 may determine an operating state of the X-ray imaging device 110. In some embodiments, the processing engine 140 may be a single server or a server group. The server group may be centralized or distributed. In some embodiments, the processing engine 140 may be local or remote. For example, the processing engine 140 may access information and/or data stored in the X-ray imaging device 110, the terminal(s) 130, and/or the storage device 150 via the network 120. As another example, the processing engine 140 may be directly connected to the X-ray imaging device 110, the terminal(s) 130 and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 300 having one or more components as illustrated in FIG. 3.

The storage device 150 may store data, instructions, and/or any other information. In some embodiments, the storage device 150 may store data obtained from the terminal(s) 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the X-ray imaging system 100 (e.g., the processing engine 140, the terminal(s) 130, etc.). One or more components of the X-ray imaging system 100 may access the data or instructions stored in the storage device 150 via the network 120. In some embodiments, the storage device 150 may be directly connected to or communicate with one or more other components of the X-ray imaging system 100 (e.g., the processing engine 140, the terminal(s) 130, etc.). In some embodiments, the storage device 150 may be part of the processing engine 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the processing engine 140 and the X-ray imaging device 110 may be integrated into one single device. However, those variations and modifications do not depart the scope of the present disclosure.

Figure 2:
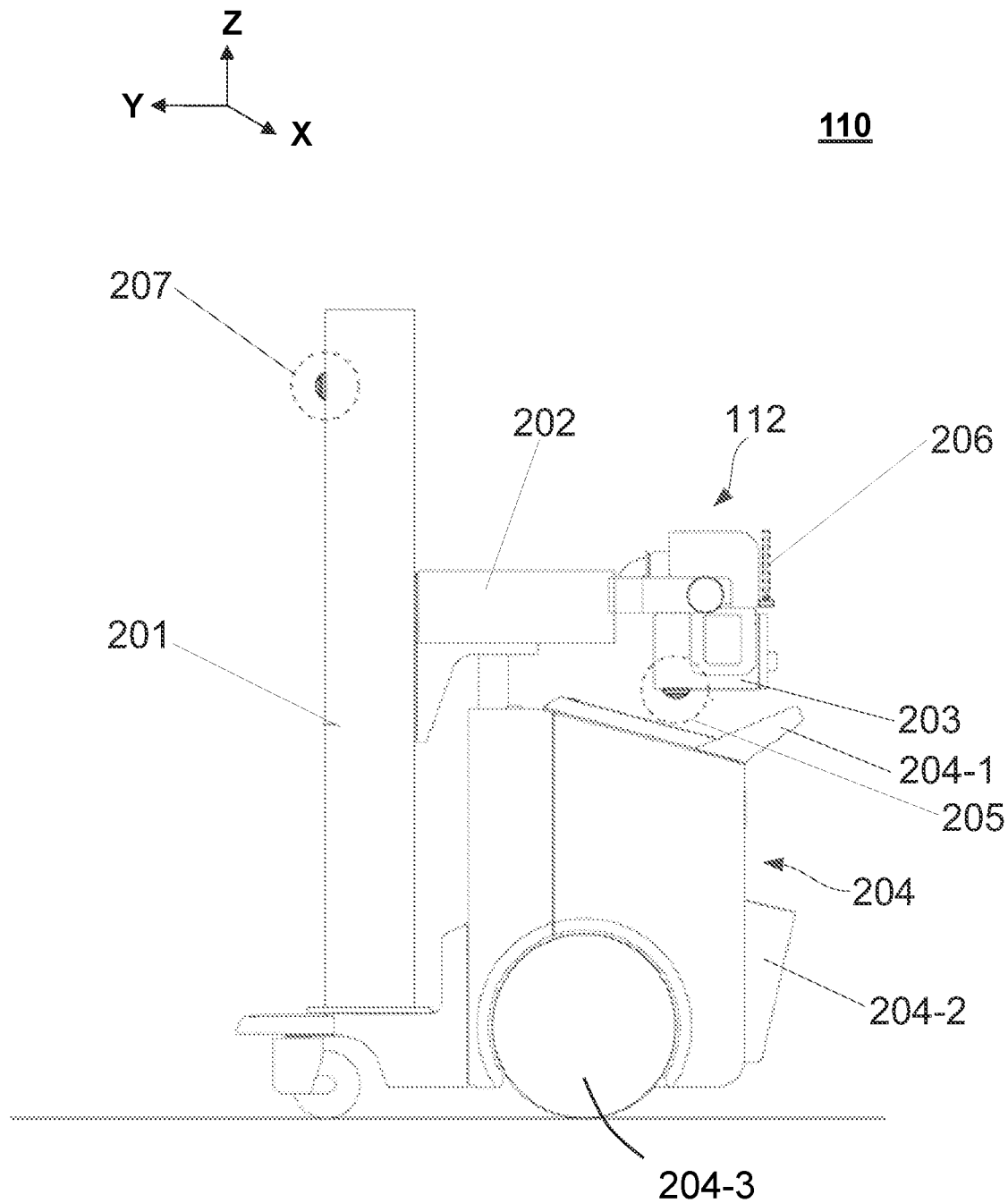
FIG. 2 is a schematic diagram illustrating an exemplary X-ray imaging device according to some embodiments of the present disclosure.

FIG. 2 is a schematic diagram illustrating an exemplary X-ray imaging device 110 according to some embodiments of the present disclosure. As shown in FIG. 2, the X-ray imaging device 110 may include a column 201, a robotic arm 202, an X-ray source 112, a trolley 204, an image acquisition device 205, a terminal 206, and a camera 207.

The column 201 may be connected to the trolley 204. In some embodiments, an end of the robotic arm 202 may be connected to the column 201, and another end of the robotic arm 202 may be connected to the X-ray source 112. The X-ray source 112 may move with the robotic arm 202. For example, the robotic arm 202 and the X-ray source 112 may move along an axis that passes through the center of the column 201 and is parallel to the Z axis as illustrated in FIG. 2. The robotic arm 202 and the X-ray source 112 may also rotate with the column 201 along an axis that passes through the center of the column 201 and is parallel to the Z-axis. In some embodiments, the robotic arm 202 may be retractable. The distance between the X-ray source 112 and the column 201 may change when the length of the robotic arm 202 changes.

In some embodiments, the X-ray source 112 may include an X-ray tube (not shown in FIG. 2) and a beam limiting device 203. The X-ray tube may be configured to emit one or more X-ray beams toward an object to be scanned. The beam limiting device 203 may be configured to control the irradiation region on the object. The beam limiting device 203 may also be configured to adjust the intensity and/or the number of the X-ray beams that irradiate on the object. In some embodiments, a handle may be mounted on the X-ray source 112. A user may grab the handle to move the X-ray source 112 to a desirable position.

The trolley 204 may include a handle 204-1, a container 204-2, and one or more wheels (e.g., a wheel 204-3). The trolley 204 may move around via the wheels. For example, a user may grab the handle 204-1 to push the trolley 204. The other components of the X-ray imaging device 110 (e.g., the column 201 and the X-ray source 112) may move with the trolley 204. The container 204-2 may be configured to accommodate one or more components of the X-ray imaging device 110. Merely by way of example, the container 240-2 may be configured to accommodate the detector (not shown in FIG. 2) of the X-ray imaging device 110. In some embodiments, the trolley 204 may be configured to move around automatically. For example, the trolley 204 may automatically move to a desirable position for the X-ray imaging device 110 to perform a scan. As another example, the trolley 204 may move in a certain direction automatically.

In some embodiments, the trolley 204 may include a workstation and/or a display (not shown in FIG. 2). The workstation may be configured to process image data collected by the X-ray imaging device 110 or an image obtained from, such as the processing engine 140, the storage device 150. The display may be configured to display data (e.g., an image generated by the processing engine 140 or the workstation).

The image acquisition device 205 may be configured to acquire image data (a video or image) of the object to be scanned. The field of view of the image acquisition device 205 may cover at least part of the field of view of the X-ray imaging device 110. In some embodiments, the video or image captured by the image acquisition device 205 may be transmitted to the terminal 206 for display. In some embodiments, the image acquisition device 205 may be mounted on the beam limiting device 203. Alternatively, the image acquisition device 205 may be connected to the robotic arm 202 via a flexible robotic arm. The field of view of the image acquisition device 205 may be adjusted by adjusting the direction and the angle of the flexible robotic arm. In some embodiments, the image acquisition device 205 may be and/or include any suitable device capable of acquiring image data. Exemplary image acquisition device 205 may include a camera (e.g., a digital camera, an analog camera), a video recorder, a mobile phone, a tablet computing device, a wearable computing device, an infrared imaging device (e.g., a thermal imaging device), or the like.

The terminal 206 may be configured to control the X-ray imaging device 110. The terminal 206 may be similar to the terminal 130 as described in connection with FIG. 1. In some embodiments, the terminal 206 may be a control panel mounted on the X-ray imaging device 110. The terminal 206 and the X-ray imaging device 110 may be integrated together. Alternatively, the terminal 206 may be separable from the X-ray imaging device 110. For example, the terminal 206 may be separated from the X-ray imaging device 110 and mounted on or accommodated in another component of the X-ray imaging device 110. For example, the terminal 206 may be mounted on the X-ray source 112 (not shown). As another example, the terminal 206 may be accommodated in the container 204-2.

In some embodiments, the terminal 206 may include a display configured to display data. For example, the display may display images captured by, such as the camera 207 and the image acquisition device 205. Additionally or alternatively, the terminal 206 may include one or more interface elements (e.g., one or more keys and/or buttons) configured to control the X-ray imaging device. For instance, a user may set the operating state and/or operating parameters of the X-ray imaging device 110 by, for example, pressing the interface elements on the terminal 206. In some embodiments, the terminal 206 may include one or more function keys, a complementary key, a display, a status bar, and a status indicator light, or the like, or any combination thereof. More descriptions regarding the terminal 206 may be found elsewhere in the present disclosure (e.g., FIGS. 8 to 16 and the relevant descriptions thereof).

The camera 207 may be mounted on the column 201 configured to capture a video or image of the scene in front of the column 201. The video or image captured by the camera 207 may be transmitted to one or more components (e.g., the terminal 206) for display. A user may get to know the road condition in front of the column 201 via the terminal 206 when he or she pushes the X-ray imaging device 110.

It should be noted that the example illustrated in FIG. 2 is provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the column 201 may be configured in any suitable manner, such as a C-shaped support, a U-shape support, a G-shape support, or the like. In some embodiments, the X-ray imaging device 110 may include one or more additional components not described, and/or without one or more components illustrated in FIG. 2. For example, the camera 207 may be omitted.

FIG. 3 is a schematic diagram illustrating exemplary hardware and/or software components of an exemplary computing device 300 on which the processing engine 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (e.g., program code) and, when executing the instructions, cause the processing engine 140 to perform functions of the processing engine 140 in accordance with techniques described herein. The computer instructions may include, for example, routines, programs, objects, components, data structures, procedures, modules, and functions, which perform particular functions described herein. For example, the processor 310 may process imaging data obtained from the X-ray imaging device 110, the terminal(s) 130, the storage device 150, and/or any other component of the X-ray imaging system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the X-ray imaging device 110, the terminal(s) 130, the storage device 150, and/or any other component of the X-ray imaging system 100. The storage 320 may be similar to the storage device 150 described in connection with FIG. 1, and the detailed descriptions are not repeated here.

The I/O 330 may input and/or output signals, data, information, etc. In some embodiments, the I/O 330 may allow a user interaction with the processing engine 140. In some embodiments, the I/O 330 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 340 may be connected to a network (e.g., the network 120) to facilitate data communications. The communication port 340 may establish connections between the processing engine 140 and the X-ray imaging device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMAX™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
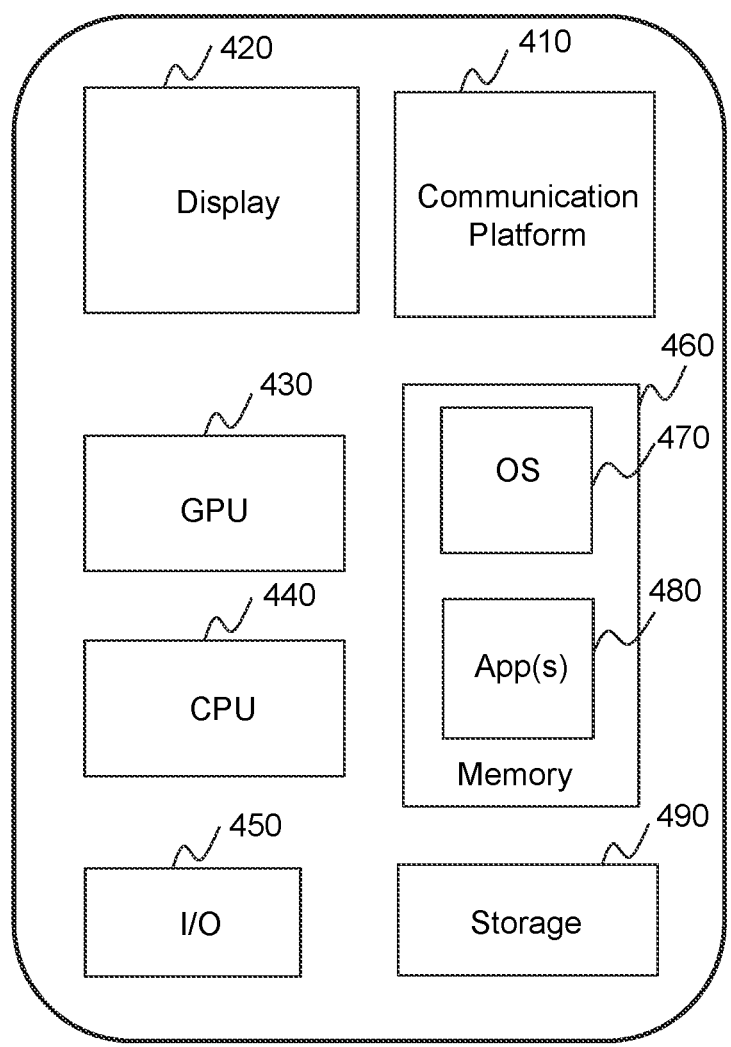
FIG. 4 is a schematic diagram illustrating exemplary hardware and/or software components of an exemplary mobile device on which a terminal may be implemented according to some embodiments of the present disclosure.

FIG. 4 is a schematic diagram illustrating exemplary hardware and/or software components of an exemplary mobile device 400 on which the terminal(s) 130 may be implemented according to some embodiments of the present disclosure. In some embodiments, the terminal 206 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing engine 140. User interactions with the information stream may be achieved via the I/O 450 and provided to the processing engine 140 and/or other components of the X-ray imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
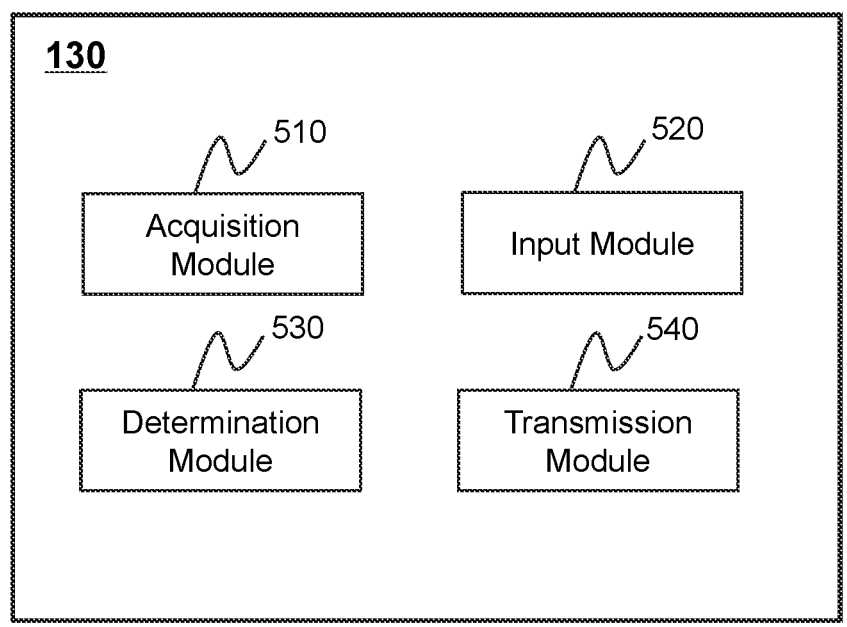
FIG. 5 is a block diagram illustrating an exemplary terminal according to some embodiments of the present disclosure.

FIG. 5 is a block diagram illustrating an exemplary terminal 130 according to some embodiments of the present disclosure. The terminal 130 may include an acquisition module 510, an input module 520, a determination module 530, and a transmission module 540.

The acquisition module 510 may be configured to obtain and/or determine an operating state of the X-ray imaging device 110. For example, the acquisition module 510 may obtain operation information of the X-ray imaging device 110, and determine the operating state of the X-ray imaging device 110 based on the operation information. The acquisition module 510 may obtain the operating state or operating information of the X-ray imaging device 110 from one or more components of the X-ray imaging system 100, such as the X-ray imaging device 110, the storage device 150, etc.

In some embodiments, the acquisition module 510 may acquire image data (e.g., a video or an image) from an image acquisition device (e.g., the image acquisition device 205) mounted on the X-ray imaging device 110. The terminal 130 may display the image data on its interface (e.g., a screen).

The input module 520 may be configured to obtain an input from a user. The input module 520 may include a keyboard, a touchscreen, a microphone, a mouse, or the like, or any combination thereof. For example, the input module 520 may include a keyboard or a touchscreen including a plurality of first keys associated with the operating states of the X-ray imaging device 110. The input module 520 may also include a second key complementary to the first keys. As another example, the input module 520 may have the touchscreen configured to receive a user's input in the form of touches, gestures, etc.

The input module 520 may also be configured to determine the input information associated with the input received. For example, the input module 520 may be configured to determine the key being pressed by a user, the time length of a key being pressed (or selected) by the user, the number of the strikes to the key by the user in a certain period.

The determination module 530 may be configured to determine whether the input satisfies a switch condition. In some embodiments, the input associated with the operating state may include a selection of the key(s) associated with the operating state of the X-ray imaging device 110. The switch condition may be associated with the time length of the key being pressed by the user and/or the number of the strikes to the key by the user in a certain period. For example, the switch condition may be that the time length of the key being pressed by the user is equal to or longer than a time threshold. As another example, the switch condition may be that the number of strikes of the key by the user in a certain period is equal to or greater than a threshold. In some embodiments, the determination module 530 may determine whether an input satisfies a switch condition to switch to a second operating state.

The transmission module 540 may be configured to transmit information and/or instructions to other components of the X-ray imaging system 100, such as the X-ray imaging device 110. For example, the transmission module 540 may transmit instructions to the X-ray imaging device 110 to control operations of the X-ray imaging device 110. In some embodiments, the transmission module 540 may communicate with one or more other modules of the terminal 130 to exchanging information and/or data.

It should be noted that the above descriptions of the terminal 130 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, the terminal 130 may include one or more other modules. For example, the terminal 130 may include a storage module to store data generated by the modules in the terminal 130. As another example, the terminal 130 may include an output module (e.g., a screen) to display information.

In some embodiments, one or more modules described may be integrated into the X-ray imaging device 110. Additionally or alternatively, the X-ray imaging device 110 may include one or more similar modules to those of the terminal 130 configured to perform at least part of the functions of the terminal 130 disclosed in this application. For example, the X-ray imaging device 110 may include a determination module similar or substantially similar to the determination module 530. The input module 520 of the terminal 130 may receive an input associated with an operating state of the X-ray imaging device 110 from a user. The transmission module 540 of the terminal 130 may transmit data and/or an instruction to the X-ray imaging device 110 according to the input. The data and/or an instruction may include input information, such as the key being pressed by the user, the time length of a key being pressed (or selected) by the user, the number of the strikes to the key by the user in a certain period. The determination module of the X-ray imaging device 110 may determine whether the input satisfies a switch condition to switch condition to switch to the operating state. Upon a determination that the input satisfies a switch condition to switch condition, the determination module may instruct the X-ray imaging device 110 to switch to the operating state.

Figure 6:
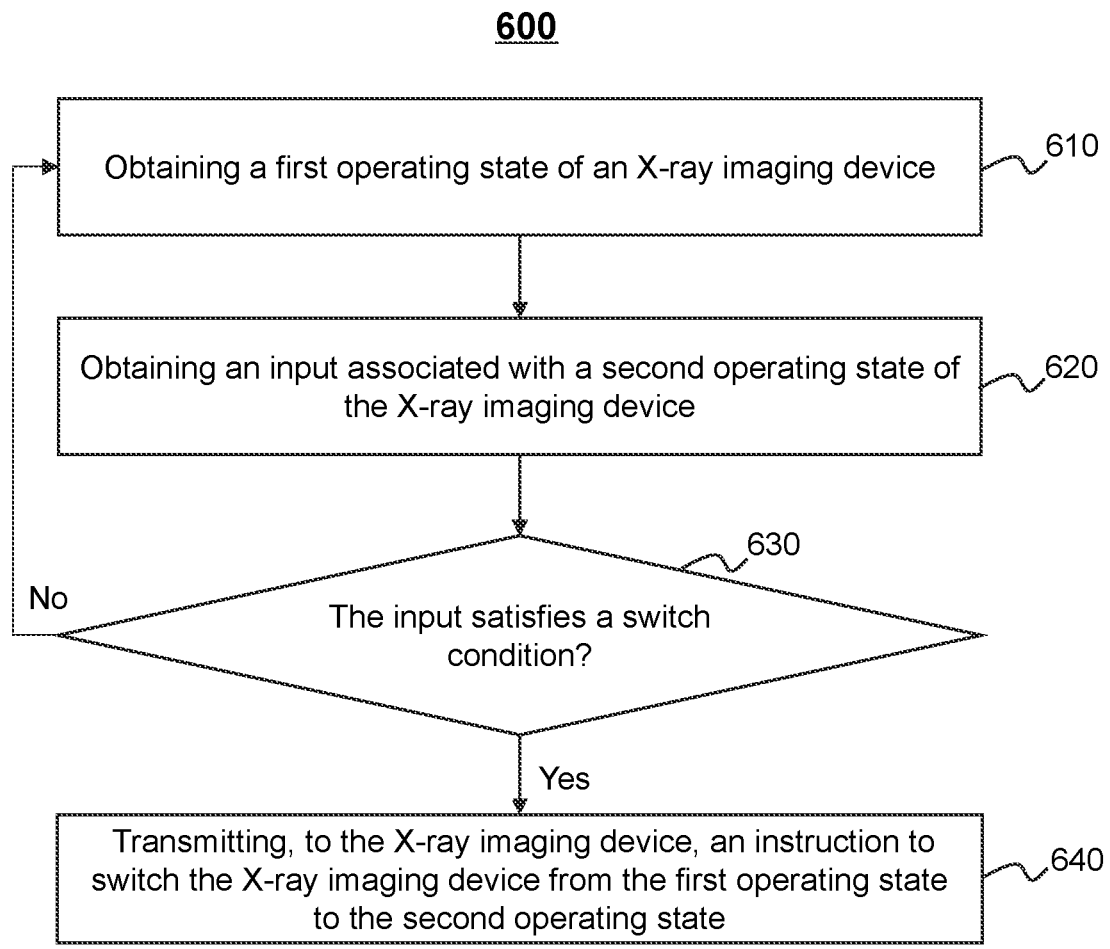
FIG. 6 is a flowchart illustrating an exemplary process for controlling an X-ray imaging device via a terminal according to some embodiments of the present disclosure.

FIG. 6 is a flowchart illustrating an exemplary process for controlling an X-ray imaging device via a terminal according to some embodiments of the present disclosure. In some embodiments, process 600 may be implemented in the X-ray imaging system 100 illustrated in FIG. 1. For example, process 600 may be stored in the storage device 150 and/or the storage apparatus (e.g., the storage 320, the storage 490) in the form of instructions, and invoked and/or executed by the terminal 130. In some embodiments, at least part of the process 600 may be performed by the processing engine 140 (implemented in, for example, the processor 310 of the computing device 300 shown in FIG. 3) and/or the terminal 130 (implemented in, for example, the CPU 440 of the mobile device 400).

In some embodiments, at least part of process 600 may be performed by the X-ray imaging device 110. For example, the X-ray imaging device 110 may include one or more modules similar to those of the terminal 130 to perform similar functions. For illustration purposes, the implement of the process 600 on the terminal 130 is described as an example.

In 610, the acquisition module 510 may obtain a first operating state of an X-ray imaging device 110. In some embodiments, the first operating state may be the operating state of the X-ray imaging device 110 at the present moment or at a defined time point reasonably close to the present moment. The acquisition module 510 may obtain and/or determine the first operating state of the X-ray imaging device 110 according to operation information of the X-ray imaging device 110. The acquisition module 510 may obtain the operation information of the X-ray imaging device 110 from one or more components of the X-ray imaging system 100, such as the X-ray imaging device 110, and/or the storage device 150.

The first operating state of the X-ray imaging device 110 may include an exposure pending state, an exposure preparation state, an exposure state, a movable state, a fixed state, a shutdown state, a sleep state, or the like. In the exposure pending state, the X-ray imaging device 110 may be waiting for a scan. In the exposure preparation state, the X-ray imaging device 110 may be preparing for a scan. For example, one or more components of the X-ray imaging device 110, such as the X-ray source 112 may be moved to a desirable position for the scan. As another example, the operating parameters (e.g., the voltage of the tube, the current of the tube) of the X-ray imaging device 110 may be adjusted according to the scan. In some embodiments, the exposure preparation state may include a state when a laser light or a light field indicator of the beam limiting device is turned on. Alternatively or additionally, the exposure preparation state may include a state when the laser light or the light field indicator is turned off.

In the exposure state, the X-ray imaging device 110 may perform a scan by emitting X-rays to the object to be scanned. In the movable state, the X-ray imaging device 110 can be movable. For example, the X-ray imaging device 110 may include a movable device (e.g., a trolley, or wheels). A user may push the X-ray imaging device 110 via the movable device. In some embodiments, the movable state may include a moving forward state, a moving backward state, a moving left state, or the like, or any combination thereof. In the fixed state, the X-ray image device 110 may be immovable. For example, the brake of the X-ray imaging device 110 may be turned on and configured to prevent the X-ray imaging device 110 from moving.

In the shutdown state, the components of the X-ray imaging device 110 may be powered off. In the sleep state, the X-ray imaging device 110 may be in a low power state and may resume itself quickly after being woken up. In some embodiments, the X-ray imaging device 110 may automatically switch to the sleep state after it remains inactive for a certain period.

In 620, the input module 520 may obtain an input associated with a second operating state of the X-ray imaging device 110. The second operating state may be different from the first operating state. The input module 520 of the terminal 130 may include a keyboard, a touchscreen, a microphone, a mouse described in connection with FIG. 5.

In some embodiments, the input module 520 may include a keyboard or a touchscreen including a plurality of first keys associated with the operating states of the X-ray imaging device 110. The first keys may also be referred to as function keys that may cause the terminal 130 to perform a certain action. The first keys may include a physical key, a touch key, or the like, or any combination thereof. The input associated with the second operating state may include a selection (or press) of one or more first keys associated with the second operating state.

In some embodiments, the input module 520 may have a microphone. The input associated with the second operating state may be a voice associated with the second operating state. In some embodiments, the input module 520 may have the touchscreen configured to receive a user's input in the form of touches, gestures, etc. For example, the input associated with the second operating state may be a gesture associated with the second operating state.

The input module 520 may also be configured to determine the input information associated with the input received. For example, the input module 520 may be configured to determine the time length of the first key being pressed by a user, the number of the strikes to the first key by the user in a certain period.

In 630, the determination module 530 may determine whether the input satisfies a switch condition. In some embodiments, the input associated with the second operating state may include a selection of the first key(s) associated with the second operating state of the X-ray imaging device 110 as described in connection with 620. The switch condition may be associated with the time length of the first key being selected by the user and/or the number of the strikes to the first key by the user in a certain period.

In some embodiments, the switch condition may be that the time length of the first key being pressed by the user is equal to or longer than a first threshold. The first threshold may be 1 second, 1.5 seconds, 2 seconds, 2.5 seconds, 3 seconds, or any suitable value. For example, only when the determination module 530 determines that the first keys associated with the second operating state is pressed for a period longer than 2 seconds, the determination module 530 may determine that the switch condition is satisfied.

In some embodiments, the switch condition may be that the number of strikes of the first key by the user in a certain period is equal to or greater than a second threshold. The second threshold may be 1, 2, 3, or any suitable value. For example, only when the determination module 530 determines that the number of strikes of the first key associated with the second operating state in 2 seconds is more than once, the determination module 530 may determine that the switch condition is satisfied.

The first threshold and/or the second threshold may be set manually or be determined by one or more components of the X-ray imaging system 100 (e.g., the determination module 530) according to different situations. The first thresholds and/or the second thresholds for different first keys associated with different operating states may be same or different.

In some embodiments, the input may be a sound or voice associated with the second operating state caused by a user. The switch condition may be that the sound or voice is inputted by a user or an authorized user. The authorized user may be a user who is authorized to control the X-ray imaging device 110. The determination module 530 may determine whether the voice is inputted by an authorized user by, such as matching the voice (or one or more characteristics thereof) with voices of a plurality of authorized users (or one or more characteristics thereof) stored in a storage device (e.g., the storage device 150, and/or the storage 320). When the voice detected is determined as being inputted by an authorized user and associated with the second operating state, the determination module 530 may determine that the switch condition is satisfied.

In some embodiments, the input module 520 may include a second key. The second key may be a complementary key a selection of which itself may not cause the terminal 130 to perform any action, but may serve as a complementary key for the first keys. For example, the switch condition may be that both the first key and second key are selected as the input. The second key and the first key may be selected simultaneously (or substantially simultaneously) to actuate the first key. Alternatively, the second key may be selected within a period (e.g., within 1 minute) before the first key is selected to actuate the first key. In some embodiments, the first key cannot be actuated or pressed down until the second key is selected (or press). For example, a user cannot select (or press) a first key if the user does not select (or press) the second key when (or before) the user selects (or presses) the functional key 810.

As another example, the switch condition may be that a sound associated with the second operating state and a selection of the second key are detected simultaneously (or substantially simultaneously) as the input. As yet another example, the switch condition may be that a gesture associated with the second operating state and a selection of the second key are detected simultaneously (or substantially simultaneously) as the input.

In response to a determination that the input associated with the second operating state satisfies the switch condition, the process 600 may proceed to 640. In 640, the transmission module 540 may transmit an instruction to the X-ray imaging device 110 to switch the X-ray imaging device 110 from the first operating state to the second operating state.

On the other hand, in response to a determination that the input associated with the second operating state does not satisfy the switch condition, the process 600 may return to 610 to re-obtain a first operating state of the X-ray imaging device 110. Alternatively, the process may return back to 620 to continue to obtain an input from a user. It should be noted that the above description of the process 600 is provided for the purposes of illustration, and not intended to limit the scope of the present disclosure. For persons having ordinary skills in the art, steps may be combined in various ways or switched with other steps. Various variations and modifications may be conducted after understanding the process. However, those variations and modifications may not depart from the spirit and scope of this disclosure. In some embodiments, the process 600 may be accomplished with one or more additional operations not described, and/or without one or more of the operations discussed. For example, step 630 may be omitted. The transmission module 540 may transmit the instruction to the X-ray imaging device 110 to switch the X-ray imaging device 110 from the first operating state to the second operating state without determining whether the input satisfies the switch condition.

In some embodiments, the input module 520 may obtain an input in 620. The input module 520 may also determine the input information associated with the input received. For example, the input module 520 may determine the key being pressed by a user, the time length of the key being pressed by the user, the number of the strikes to the key by the user in a certain period.

In 630, the determination module 530 may determine whether the input satisfies a switch condition to switch to a second operating state. In some embodiments, the determination module 530 may determine whether the input is associated with the second operating state. For example, the determination module 530 may determine whether the input includes a selection of a first key associated with the second operating state. Upon a determination that the input includes the selection of the first key associated with the second operating state, the determination module 530 may then determine whether the input satisfies a condition to switch to the second operating state. For example, the determination module 530 may determine whether the time length of the first key being pressed by the user is equal to or longer than a first threshold, or the number of the strikes of the first key by the user in a certain period is equal to or greater than a second threshold. Upon a determination that the time length of the first key being pressed is equal to or longer than the first threshold, or the number of the strikes of the first key in the certain period is equal to or greater than the second threshold, the determination module 530 may determine that the switch condition to switch to the second operating state is satisfied.

In some embodiments, the terminal 130 may include a configurable interface. The interface of the terminal 130 may automatically be configured or adjusted according to the operation state of the X-ray imaging device 110. In some embodiments, the terminal 130 may have an interface corresponding to the second operating state of the X-ray imaging device 110 (also referred as the first interface). The terminal 130 may display the interface when the X-ray imaging device 110 operates in the first operating state, and a user may switch the X-ray imaging device 110 to the second operating state conveniently. For example, when the X-ray imaging device 110 operates in the first operating state, the terminal 130 may display a key corresponding to the second operating state of the X-ray imaging device 110. In some embodiments, the determination module 520 or the terminal 130 may determine whether the X-ray imaging device 110 operates in the first operating state. In response to a result of the determination that the X-ray imaging device 110 operates in the first operating state, the terminal 130 may display the first interface corresponding to the second operating state.

Additionally or alternatively, the X-ray imaging device 110 may include a third operating state. The terminal 130 may further have an interface corresponding to the third operating state of the X-ray imaging device 110 (also referred to as the second interface). Upon the determination that the first input satisfies the switch condition as described in connection with step 630, the transmission module 540 may transmit an instruction to the terminal 130 to direct the terminal 130 to switch from the first interface to the second interface. For example, the key corresponding to the second operating state may be marked inactive or disappear in the interface of the terminal 130, and the terminal 130 may display the key corresponding to the third operating state.

Figure 7:
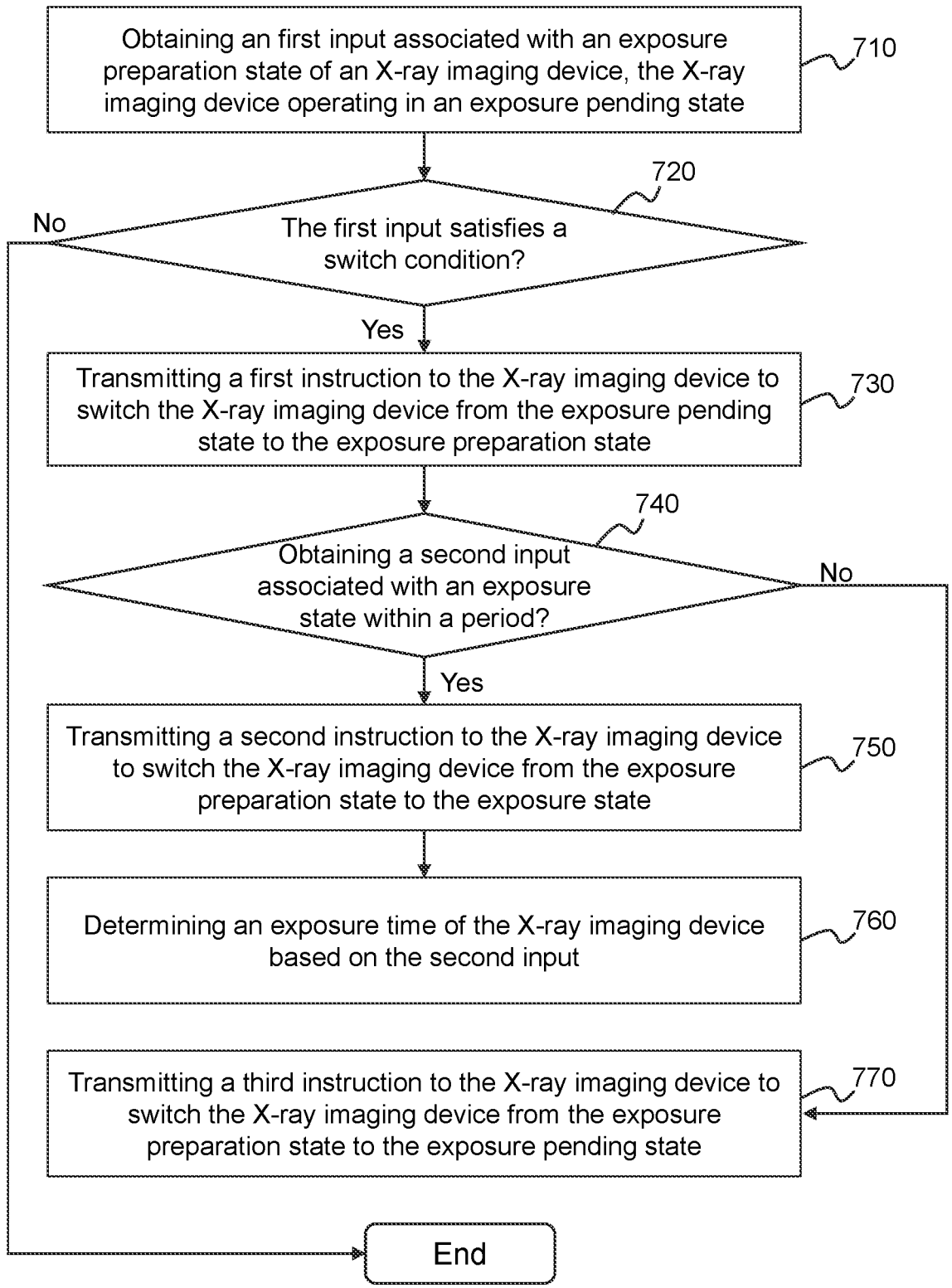
FIG. 7 is a flowchart illustrating an exemplary process for controlling an X-ray imaging device via a terminal according to some embodiments of the present disclosure.

FIG. 7 is a flowchart illustrating an exemplary process for controlling an X-ray imaging device via a terminal according to some embodiments of the present disclosure. In some embodiments, process 700 may be implemented in the X-ray imaging system 100 illustrated in FIG. 1. For example, process 700 may be stored in the storage device 150 and/or the storage apparatus (e.g., the storage 320, the storage 490) in the form of instructions, and invoked and/or executed by the terminal 130. In some embodiments, at least part of process 700 may be performed by the processing engine 140 (implemented in, for example, the processor 310 of the computing device 300 shown in FIG. 3) and/or the terminal 130 (implemented in, for example, the CPU 440 of the mobile device 400).

In some embodiments, at least part of process 700 may be performed by the X-ray imaging device 110. For example, the X-ray imaging device 110 may include one or more modules similar to those of the terminal 130 to perform similar functions. For illustration purposes, the implement of the process 700 by the terminal 130 is described as an example. In some embodiments, process 700 may be an embodiment of process 600. The operating state of the X-ray imaging device 110 may include an exposure pending state, an exposure preparation state, and an exposure state. The first operating state of the X-ray imaging device 110 may be the exposure pending state.

In some embodiments, the interface of the terminal 130 may be adjusted according to the operating state of the X-ray imaging device 110 as described elsewhere in this disclosure. When the X-ray imaging device 110 operates in the exposure pending state, the terminal 130 may display an interface corresponding to the exposure preparation state of the X-ray imaging device 110. For example, the terminal 130 may display a key associated with the exposure preparation state when the X-ray imaging device 110 operates in the exposure pending state. For brevity, the key associated with the exposure preparation state may be referred to as an exposure preparation key. As another example, the terminal 130 may display a plurality of keys corresponding to different operating states of the X-ray imaging device 110. When the X-ray imaging device 110 operates in the exposure pending state, the exposure preparation key may be marked as active, and the other keys may be marked as inactive.

In 710, the input module 520 may obtain a first input associated with an exposure preparation state of the X-ray imaging device 110. The first input associated with the exposure preparation state may include a selection of the exposure preparation key, a sound and/or gesture associated with the exposure preparation state, or the like. The first input may be similar to the input in step 620, and the detailed descriptions thereof are not repeated herein.

In 720, the determination module 530 may determine whether the first input associated with the exposure preparation state satisfies a switch condition associated with the exposure preparation state. In some embodiments, the switch condition may be associated with the time length of the exposure preparation key being pressed by the user and/or the number of the strikes to the exposure preparation key by the user in a certain period. For example, the switch condition may be that the time length of the exposure preparation key being pressed is equal to or longer than a first threshold. In some embodiments, the first threshold may range from 30 milliseconds to 5 seconds. As another example, the switch condition may be that the number of strikes of the exposure preparation key by the user in a certain period is equal to or greater than a second threshold. In some embodiments, the switch condition may be that the exposure preparation key is stroked by the user more than once within a certain period. The certain period may range from 0.5 seconds to 2 seconds. In some embodiments, the switch condition may be that the input includes a selection of the exposure preparation key and a selection of a second key (e.g., a complementary key). Step 720 may be performed similarly with step 630, and the detailed descriptions thereof are not repeated herein.

In response to a determination that the first input does not satisfy the switch condition, the X-ray imaging device 110 may still operate in the exposure pending state, and the process 700 may be terminated. On the other hand, in response to a determination that the first input satisfies the switch condition, the process 700 may proceed to 730. In 730, the transmission module 540 may transmit a first instruction to the X-ray imaging device 110 to switch the X-ray imaging device 110 from the exposure pending state to the exposure preparation state. The operating parameters of the X-ray imaging device 110 may be adjusted accordingly to prepare for a scan.

In some embodiments, when the first input satisfies the switch condition and/or the X-ray imaging device 110 switches to the exposure preparation state, the terminal 130 may change its interface from the one corresponding to the exposure preparation state to another one corresponding to the exposure state. For example, the exposure preparation key may be marked inactive or disappear, and the terminal 130 may display a key associated with the exposure state. For brevity, the key associated with the exposure state may be referred to as an exposure key.

In 740, the determination module 530 may determine whether a second input associated with an exposure state of the X-ray imaging device 110 is obtained within a period. The second input may be acquired by the input module 520. The second input may include a selection of the exposure key, a sound, and/or gesture associated with the exposure state of the X-ray imaging device 110. The second input may be similar to the input as described in connection with step 620, and the detailed descriptions thereof are not repeated here. The period may be set manually or be determined by one or more components of the X-ray imaging system 100 (e.g., the determination module 530) according to different situations. The period may be 1 second, 2 seconds, 5 seconds, 10 seconds, 15 seconds, or any suitable value. In some embodiments, the period may range from 2 seconds to 6 seconds.

In response to a determination that the second input associated with the exposure state is obtained within the period, the process 700 may proceed to 750. In 750, the transmission module 540 may transmit a second instruction to the X-ray imaging device 110 to switch the X-ray imaging device 110 from the exposure preparation state to the exposure state. The X-ray imaging device 110 may perform a scan by emitting X-rays to the object to be scanned.

On the other hand, upon a determination that the second input associated with the exposure state is not obtained within the period, the process 700 may proceed to 770. In 770, the transmission module 540 may transmit a third instruction to the X-ray imaging device 110 to switch the X-ray imaging device 110 from the exposure preparation state back to the exposure pending state. In some embodiments, when the X-ray imaging device 110 switches back to the exposure pending state, the interface of the terminal 130 may switch back to the interface corresponding to the exposure preparation state. For example, the terminal 130 may display the exposure preparation key.

In 760, the determination module 530 may determine an exposure time of the X-ray imaging device 110 based on the second input associated with the exposure state. In some embodiments, the second input may be a selection of the exposure key. The exposure time may be determined based on the time length of the exposure key being selected. For example, the exposure time may be equal to or substantially equal to the selection period of the exposure key. In 740, the transmission module 540 may transmit the instruction to direct the X-ray imaging device 110 to operate in the exposure state when (or immediately after) the exposure key is selected within the period. The transmission module 540 may transmit an instruction to the X-ray imaging device 110 to stop emitting X-rays when (or immediately after) the exposure key is released.

As another example, the exposure time may be determined based on the time length of the exposure key being selected and a period threshold. The transmission module 540 may transmit the instruction to the X-ray imaging device 110 to switch to the exposure state if the time length of the selection of the exposure key is equal to or exceeds the period threshold. The threshold may be 1 second, 2 seconds, or any suitable value. Merely by way of example, if the period threshold is 1 second, the transmission module 540 may transmit the instruction to the X-ray imaging device 110 to switch to the exposure state when the exposure key is selected or pressed for 1 second or longer. The transmission module 540 may transmit an instruction to the X-ray imaging device 110 to stop emitting X-rays when (or immediately after) the exposure key is released.

In some embodiments, the second input may be a selection of the exposure key and a second key (e.g., a complementary key). The exposure time may be determined based on the time length of the exposure key and the complementary key being selected (or pressed) simultaneously. Alternatively, the exposure time may be determined based on the time length of the exposure key and the complementary key being selected (or pressed) simultaneously and a period threshold.

In some embodiments, the second input may be a gesture and/or a sound associated with the exposure state. The exposure time may be determined based on the duration of the gesture and/or the sound. Alternatively, the exposure time may be determined based on the duration of the gesture and/or the sound, and a period threshold. It should be noted that the above description of the process 700 is provided for the purpose of illustration, and not intended to limit the scope of the present disclosure. For persons having ordinary skills in the art, steps may be combined in various ways or switched with other steps. Various variations and modifications may be conducted after understanding the process. However, those variations and modifications may not depart from the spirit and scope of this disclosure. In some embodiments, the process 700 may be accomplished with one or more additional operations not described, and/or without one or more of the operations discussed. For example, step 720 may be omitted. The transmission module 540 may transmit the instruction to the X-ray imaging device 110 to switch the X-ray imaging device 110 from the exposure pending state to the exposure preparation state without determining whether the first input satisfies the switch condition. As another example, step 760 may be omitted. The X-ray imaging device 100 may perform a scan based on a preset exposure time.

In some embodiments, after step 740, the determination module 530 may determine whether the second input associated with the exposure state satisfies a switch condition associated with the exposure state. When the determination module 530 determines that the second input satisfies the switch condition associated with the exposure state, the process 700 may proceed to step 750 to transmit the second instruction to the X-ray imaging device 110 to switch the X-ray imaging device 110 from the exposure preparation state to the exposure state. The switch condition associated with the exposure state may be similar to that associated with the exposure preparation state as described in connection with 720. Table 1 illustrates exemplary switch conditions associated with the exposure preparation state, switch conditions associated with the exposure state, and time points when the transmission module 540 transmits an instruction to the X-ray imaging device 110 to stop emitting X-rays.

TABLE 1

| The switch condition associated with the exposure preparation state | The switch condition associated with the exposure state | The time point to stop emitting X-rays |
|---|---|---|
| The exposure preparation key and a second key are selected simultaneously | The exposure key and a second key are selected simultaneously | The exposure key and a second key are released simultaneously |
| The exposure preparation key and a second key are selected simultaneously | The exposure key and a second key are selected simultaneously | The exposure key is released |
| The exposure preparation key and a second key are selected simultaneously | The time length of the exposure key being selected is longer than a threshold | The exposure key is released |

TABLE 1-continued

| The switch condition associated with the exposure preparation state | The switch condition associated with the exposure state | The time point to stop emitting X-rays |
|---|---|---|
| The exposure preparation key and a second key are selected simultaneously | The exposure key is selected | / |
| The exposure preparation key and a second key are selected simultaneously | The number of strikes of the exposure key is greater than a threshold | / |
| The time length of the exposure preparation key being selected is longer than a threshold | The exposure key and a second key are selected simultaneously | The exposure key and a second key are released simultaneously |
| The time length of the exposure preparation key being selected is longer than a threshold | The exposure key and a second key are selected simultaneously | The exposure key is released |
| The exposure preparation key is selected | The exposure key and a second key are selected simultaneously | The exposure key and a second key are released simultaneously |
| The exposure preparation key is selected | The exposure key and a second key are selected simultaneously | The exposure key is released |
| The number of strikes of the exposure preparation key is greater than a threshold | The exposure key and a second key are selected simultaneously | The exposure key and a second key are released simultaneously |
| The number of strikes of the exposure preparation key is greater than a threshold | The exposure key and a second key are selected simultaneously | The exposure key is released |

Figure 8:
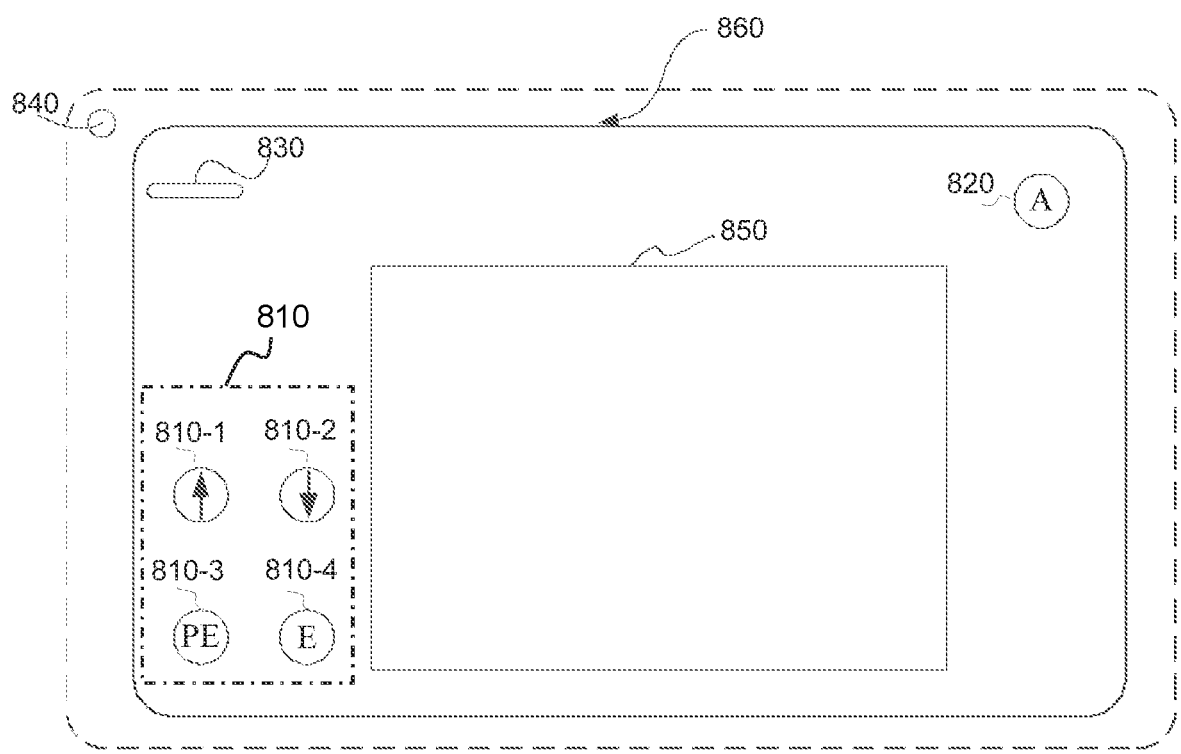
FIG. 8 is a schematic diagram illustrating an exemplary terminal according to some embodiments of the present disclosure.

FIG. 8 is a schematic diagram illustrating an exemplary terminal 800 according to some embodiments of the present disclosure. The terminal 800 may be an embodiment of the terminal 130 and/or the terminal 206 as described elsewhere in this disclosure (e.g., FIGS. 1 and 2 and the relevant descriptions thereof). In some embodiments, the terminal 800 may control the X-ray imaging device 110 by implementing the process 600 and/or the process 700.

In some embodiments, the terminal 800 may be implemented in the mobile device 400 (e.g., in the form of a tablet computer). The size and/or the shape of the terminal 800 may be adjusted according to different demand. In some embodiments, the ratio of the length to the width of the terminal 800 may be adjusted according to different demand. For example, the length of terminal 800 may be larger than its width as shown in FIG. 8.

The terminal 800 may include an interface 860 and a status indicator light 840. In some embodiments, the interface 860 may include a first region and a second region. The first region may be a region where a user usually touches when he or she holds the terminal 800. For example, the first region may include the bottom-left region and/or the bottom-right region of the interface 860. The second region may be a region where a user does not usually touch when he or she holds the terminal 800. For example, the second region may be the upper region of the interface 860. In some embodiments, the second region may be the region other than the first region on the interface 860. In some embodiments, the interface 860 may display an image or video of an object to be scanned. The image or video may be captured by an image acquisition device (e.g., the image acquisition device 205) mounted on the X-ray imaging device.

The interface 860 may include one or more interface elements. For example, the interface 860 may include one or more function keys 810, a complementary key 820, a display 850, and a status bar 830. In some embodiments, at least one of the function keys 810 may be a physical key.

The interface 860 may also include a touchscreen. In some embodiments, at least one of the function keys 810 and the complementary key 820 may be a soft key displayed on the touchscreen. A user may input information and/or instructions via selecting or pressing the function keys 810 and/or the complementary key 820.

The selection by a user of a function key 810 may cause the terminal 800 to perform a certain action. For example, the function key 810 may include one or more first keys associated with operating states of an X-ray imaging device 110 as described in connection with FIG. 6. The selection of the function key 810 inputted by a user may cause the terminal 800 to control the operating states of the X-ray imaging device 110. In some embodiments, the selection of the function key 810 may cause the terminal to control the operating state of the X-ray imaging device 110 only when it satisfies a switch condition. For example, only when the time length of the function key 810 being selected is equal to or greater than a time threshold, the terminal 800 may direct the X-ray imaging device 110 to operate in the corresponding operating state. More descriptions regarding the switch condition may be found elsewhere in the present disclosure (e.g., FIGS. 6 and 7, and the relevant descriptions thereof).

In some embodiments, the function key 810 may include a moving forward key 810-1, a moving backward key 810-2, an exposure preparation key 810-3, and an exposure key 810-4. The selection of the moving forward key 810-1 or the moving backward key 810-2 may cause the terminal 800 to direct the X-ray imaging device 110 to move forward or move backward. For example, the terminal 800 may transmit an instruction to direct the X-ray imaging device 110 to release a brake and move forward or backward. The selection of the exposure preparation key 810-3 may cause the terminal 800 to direct the X-ray imaging device 110 to prepare for a scan (e.g., to adjust the operating parameters for the scan). The selection of the exposure key 810-4 may cause the terminal 800 to direct the X-ray imaging device 110 to perform a scan by emitting X-rays. In some embodiments, the function keys 810 may be located in the first region the first region (e.g., the bottom-left region) of the interface 860 as illustrated in FIG. 8.

It should be noted that the function keys 810 illustrated in FIG. 8 are merely provided for the purposes of illustration and not intended to limit the scope of the present disclosure. The terminal 800 may include any number of function keys 810. For example, the function keys 810 may include one or more function keys associated with other operating states of the X-ray imaging device 110. In some embodiments, the function keys 810 may include an exposure pending key associated with the exposure pending state, a key associated with the fixed state, a key associated with the movable state, or the like, or any combination thereof. As another example, the function keys 810 may be in any region of the interface 860, such as the bottom-right region of the interface 860. The locations of the function keys 810 may be set manually by a user or be automatically adjusted according to different situations.

The selection of the complementary key 820 by itself may not cause the terminal 800 to perform a certain action and serve as a complementary key for the function keys 810. In some embodiments, a user may have to select (or press) a function key 810 and the complementary key 820 at the same or substantially same time to actuate the function key 810. For example, the user may select (or press) the exposure preparation key 810-3 and the complementary key 820 at the same or substantially same time so that the terminal 800 may transmit an instruction to direct the X-ray imaging device 110 to operate in the exposure preparation state.

As another example, the user may select the exposure key 810-4 and the complementary key 820 at the same or substantially same time so that the terminal 800 may transmit an instruction to direct the X-ray imaging device 110 to operate in the exposure state. The exposure time of the X-ray imaging device 110 may be determined based on the time length of the exposure key 810-4 being selected and/or the time length of the complementary key 820 being selected. Details regarding the determination of the exposure time may be found elsewhere in the present disclosure (e.g., FIG. 7 and the relevant descriptions thereof).

In some embodiments, the function keys 810 cannot be actuated or press down until the complementary key 820 is selected (or pressed). For example, a functional key 810 cannot be actuated if the user does not select (or press) the additional key 820 when (or before) the user selects (or presses) the functional key 810.

The terminal may have any number of the complementary keys 820. Different function keys 810 may correspond to a same or different complementary keys 820. The complementary key 820 may be in any region of the interface 860. For example, the complementary key 820 may be in the second region (e.g., the upper-right region) of the interface 860 as illustrated in FIG. 8. The location of the complementary key 820 may be set manually by a user or be atomically adjusted according to different situations.

The status bar 830 and/or the status indicator light 840 may be configured to indicate the status of one or more components of the X-ray imaging system 100, such as the X-ray imaging device 110 or the terminal 800. In some embodiments, when the terminal 800 directs the X-ray imaging device 110 to operate in the exposure preparation state, the status bar 830 may indicate the preparation progress of the X-ray imaging device 110. The X-ray imaging device 110 may transmit a signal to the transmission module 540 of the terminal 800 to indicate its preparation progress.

The terminal 800 may display the preparation progress of the X-ray imaging device 110 via the status bar 830 based on the signal.

For example, the status bar 830 may be in red when the X-ray imaging device 110 is not preparing for a scan. When the X-ray imaging device 110 begins to prepare for the scan, a portion of the status bar 830 may turn to green. The green portion may grow according to the preparation progress of the X-ray imaging device 110. Alternatively, the status bar 830 may gradually turn from red to green according to the preparation progress. The status bar 830 may turn green when the X-ray imaging device 110 finishes the preparation.

In some embodiments, the status indicator light 840 may indicate the communication status between the terminal 800 and the X-ray imaging device 110. When the distance between the terminal 800 and the X-ray imaging device 110 is within a threshold, the terminal 800 may be wirelessly connected to and communicated with the X-ray imaging device 110. The status indicator light 840 may be turned up to inform a user that the terminal 800 and the X-ray imaging device 110 are in communication with each other. The user may control the X-ray imaging device 110 via the terminal 800.

It should be noted that the terminal 800 as illustrated in FIG. 8 is provided for the purpose of illustration, and not intended to limit the scope of the present disclosure. For persons having ordinary skills in the art, steps may be combined in various ways or switched with other steps. Various variations and modifications may be conducted after understanding the process. However, those variations and modifications may not depart from the spirit and scope of this disclosure. In some embodiments, the terminal 800 may include one or more additional components not described, and/or without one or more components as illustrated in FIG. 8. For example, the status bar 830, the status indicator light 840, or the complementary key 820 may be omitted. As another example, the terminal 800 may further include other input devices, such as a microphone. In some embodiments, the interface elements on the interface 860, such as the function keys 810, the display 850, and the complementary key 820 may be arranged in any configuration other than that shown in FIG. 8.

Figure 9:
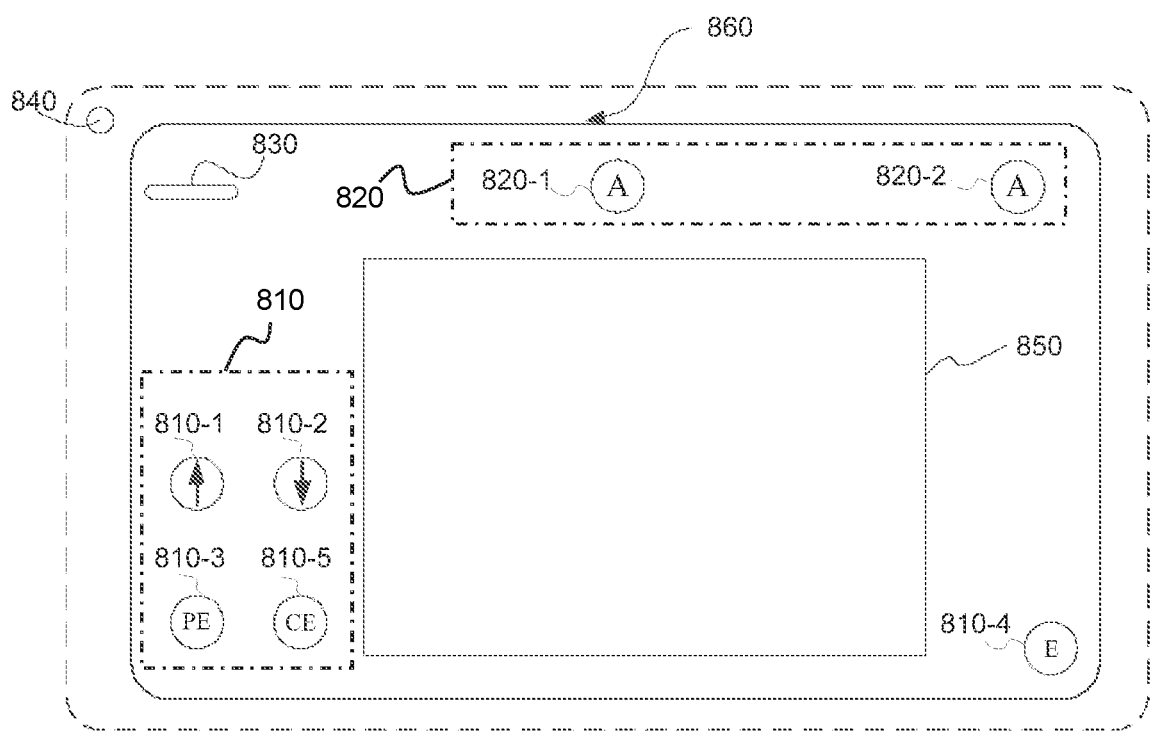
FIG. 9 is a schematic diagram illustrating an exemplary terminal according to some embodiments of the present disclosure.

FIG. 9 is a schematic diagram illustrating an exemplary terminal 900 according to some embodiments of the present disclosure. The terminal 900 may be similar to the terminal 800, except for certain components or features.

The terminal 900 may include a plurality of complementary keys 820. Different complementary keys 820 may correspond to a same or different functional keys 810. As shown in FIG. 9, the terminal 900 may include a complementary key 820-1 and a complementary key 820-2. The two complementary keys 820 may correspond to a same functional keys 810. Additionally or alternatively, the two complementary keys 820 may correspond to different functional keys 810. For example, a user may press the moving forward key 810-1 and the complementary key 820-1 simultaneously to actuate the moving forward key 810-1, and press the moving backward key 810-2 and the complementary key 820-2 to actuate the moving backward key 810-2. The terminal 900 may further include a cancel key 810-5. The selection of the cancel key 810-5 may cause the terminal 900 to direct the X-ray imaging device 110 to stop emitting X-rays.

Figure 10:
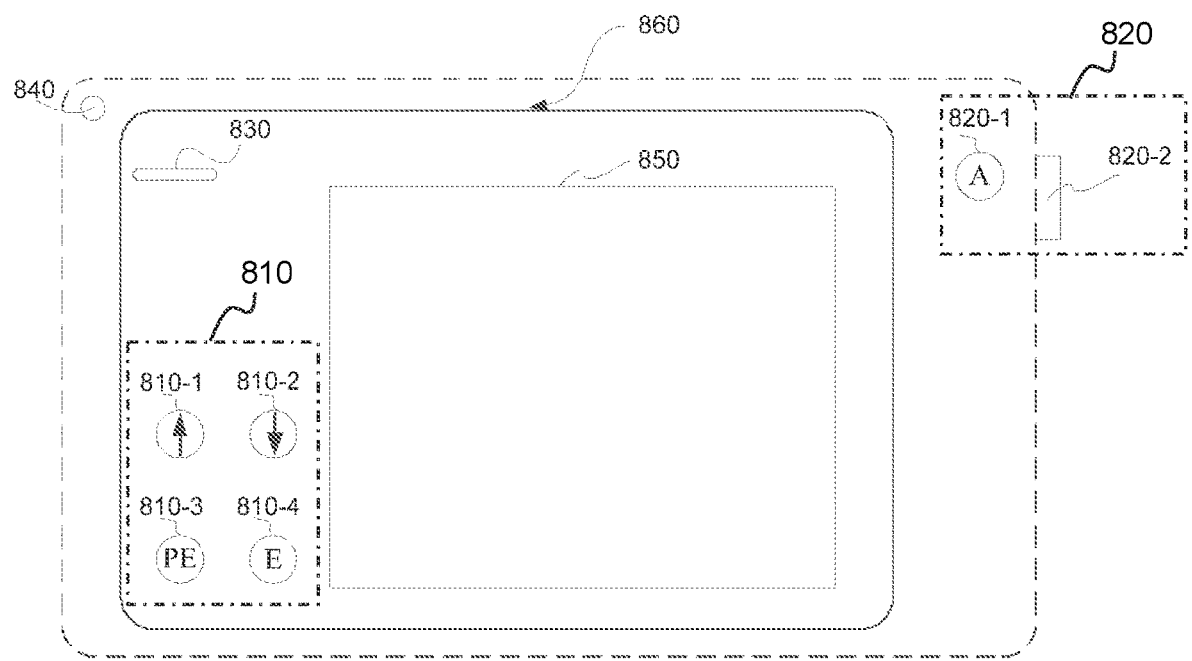
FIG. 10 is a schematic diagram illustrating an exemplary terminal according to some embodiments of the present disclosure.

FIG. 10 is a schematic diagram illustrating an exemplary terminal 1000 according to some embodiments of the present disclosure. The terminal 1000 may be similar to the terminal 800, except for certain components or features.

As shown in FIG. 10, the terminal 1000 may include a complementary key 820 located in a region outside of the interface 860. For example, the terminal 1000 may include a complementary key 820-1 on the front side of the terminal 1000 and/or a complementary key 820-2 on the right side of the terminal 1000. In some embodiments, the complementary key 820 may be a physical key.

Figure 11:
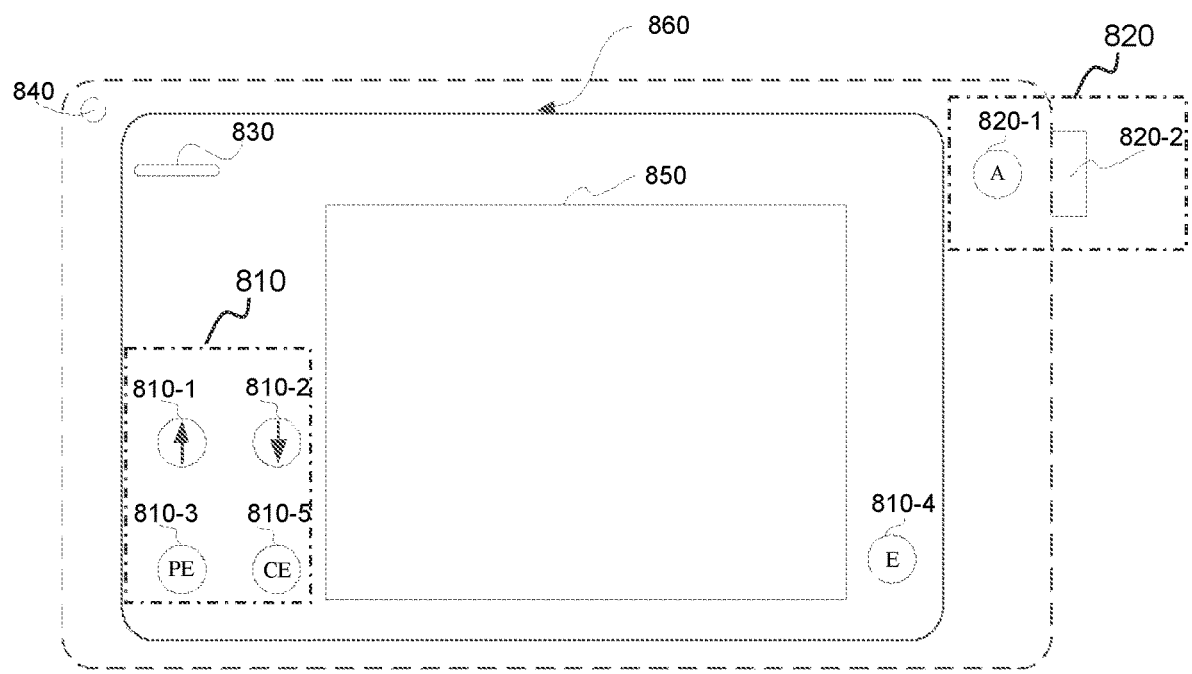
FIG. 11 is a schematic diagram illustrating an exemplary terminal according to some embodiments of the present disclosure.

FIG. 11 is a schematic diagram illustrating an exemplary terminal 1100 according to some embodiments of the present disclosure. The terminal 1100 may be similar to the terminal 1000, except for certain components or features. As shown in FIG. 11, the terminal 1100 may further include a cancel key 810-5. The exposure key 810-4 may be arranged on the bottom-right portion of the interface 860.

Figure 12A:
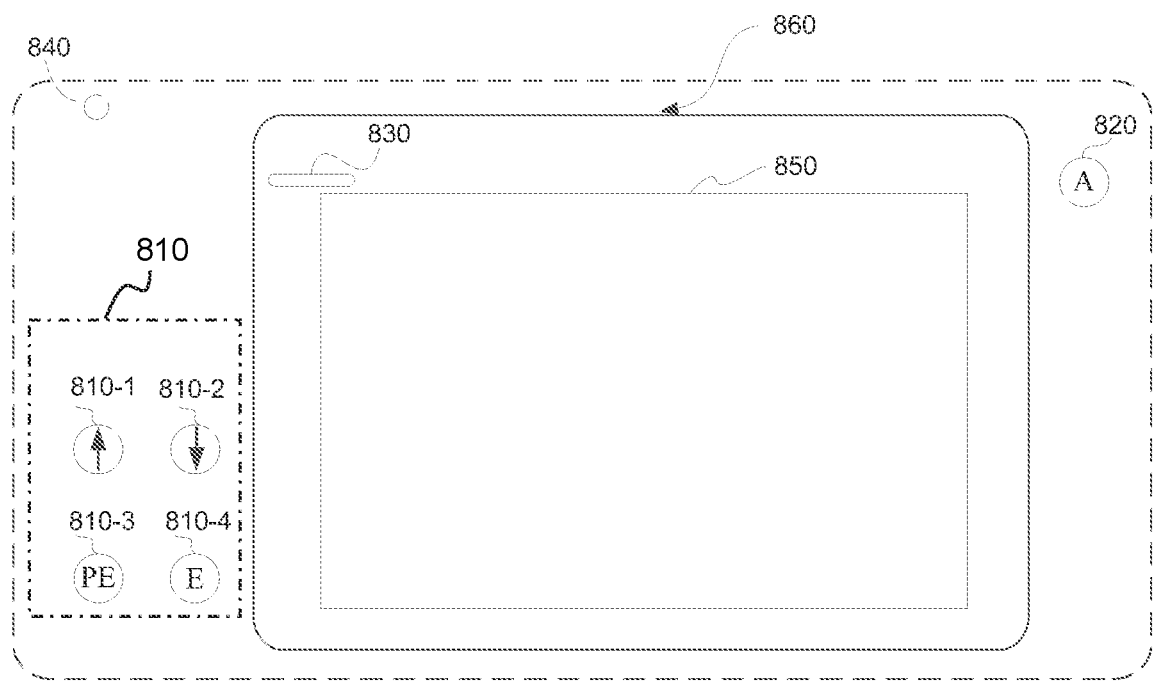
FIG. 12A is a schematic diagram illustrating an exemplary terminal according to some embodiments of the present disclosure.
Figure 12B:
FIG. 12B is the side view of an exemplary terminal according to some embodiments of the present disclosure.

FIGS. 12A and 12B are schematic diagrams illustrating an exemplary terminal 1200 according to some embodiments of the present disclosure. FIG. 12A illustrates the front view of the terminal 1200, and FIG. 12B illustrates the side view of the terminal 1200. The terminal 1200 may be similar to the terminal 800, except for certain components or features. For example, the function keys 810 and the complementary key 820 of the terminal 1200 may be physical keys.

In some embodiments, the function key 810 and/or complementary key 820 may be raised keys (or buttons) from the flat surface of the terminal 1200. For example, as illustrated in FIG. 12B, the exposure key 810-4 and the complementary key 820 may be raised buttons. The height of the function keys 810 may be different from that of the complementary key 820. For example, the height of the exposure key 810-4 may be greater than that of the complementary key 820 as shown in FIG. 12B. As another example, the terminal 1200 may include a groove (not shown in FIG. 12B). The complementary key 820 may be accommodated in the groove. The top surface of the complementary key 820 may be lower than the flat surface of the terminal 1200.

Figure 13A:
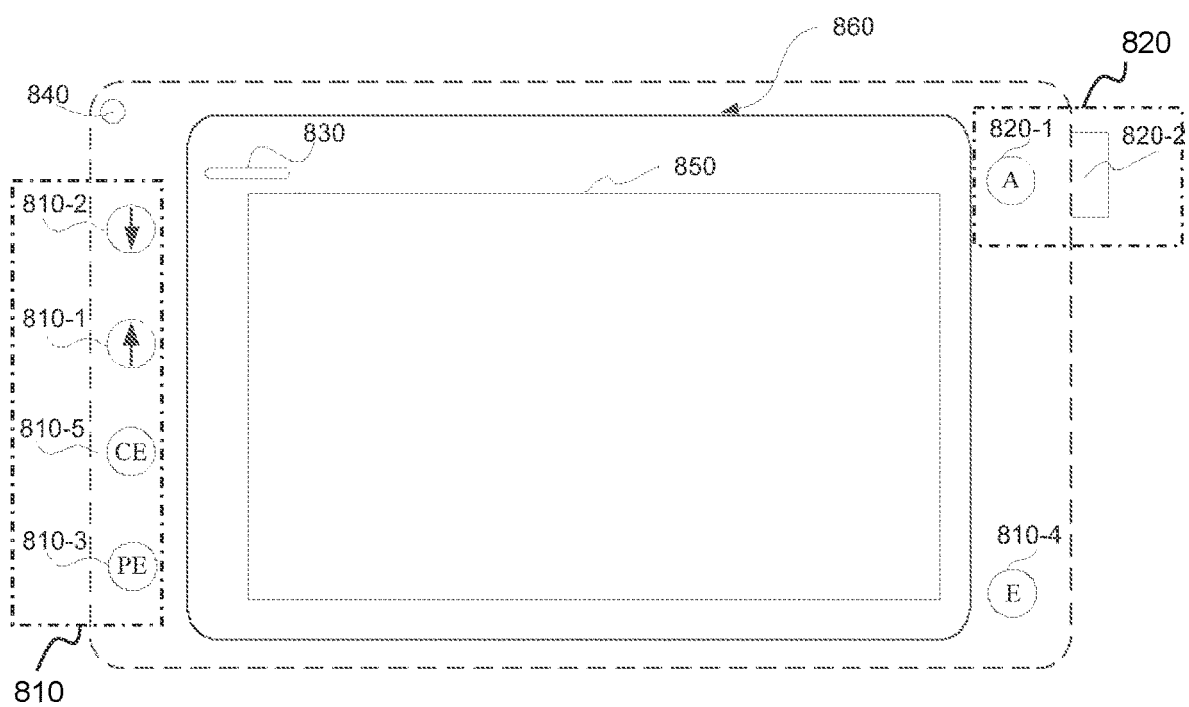
FIG. 13A is a schematic diagram illustrating an exemplary terminal according to some embodiments of the present disclosure.
Figure 13B:
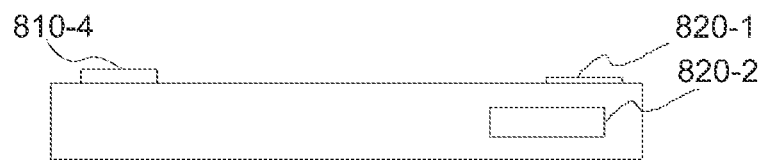
FIG. 13B is the side view of an exemplary terminal according to some embodiments of the present disclosure.

FIGS. 13A and 13B are schematic diagrams illustrating an exemplary terminal 1300 according to some embodiments of the present disclosure. FIG. 13A illustrates the front view of the terminal 1300, and FIG. 13B illustrates the side view of the terminal 1300. The terminal 1300 may be similar to the terminal 1100 and/or the terminal 1200, except for certain components or features.

As shown in FIG. 13A, the functional keys 810 of the terminal 1300 are arranged in an array. The exposure key 810-4 may be a physical key located in a region outside of the interface 860. The exposure key 810-4, the complementary key 820-1, and/or the complementary key 820-2 may be raised keys (or buttons) from the flat surface of the terminal 1300 as illustrated in FIG. 13B.

Figure 14:
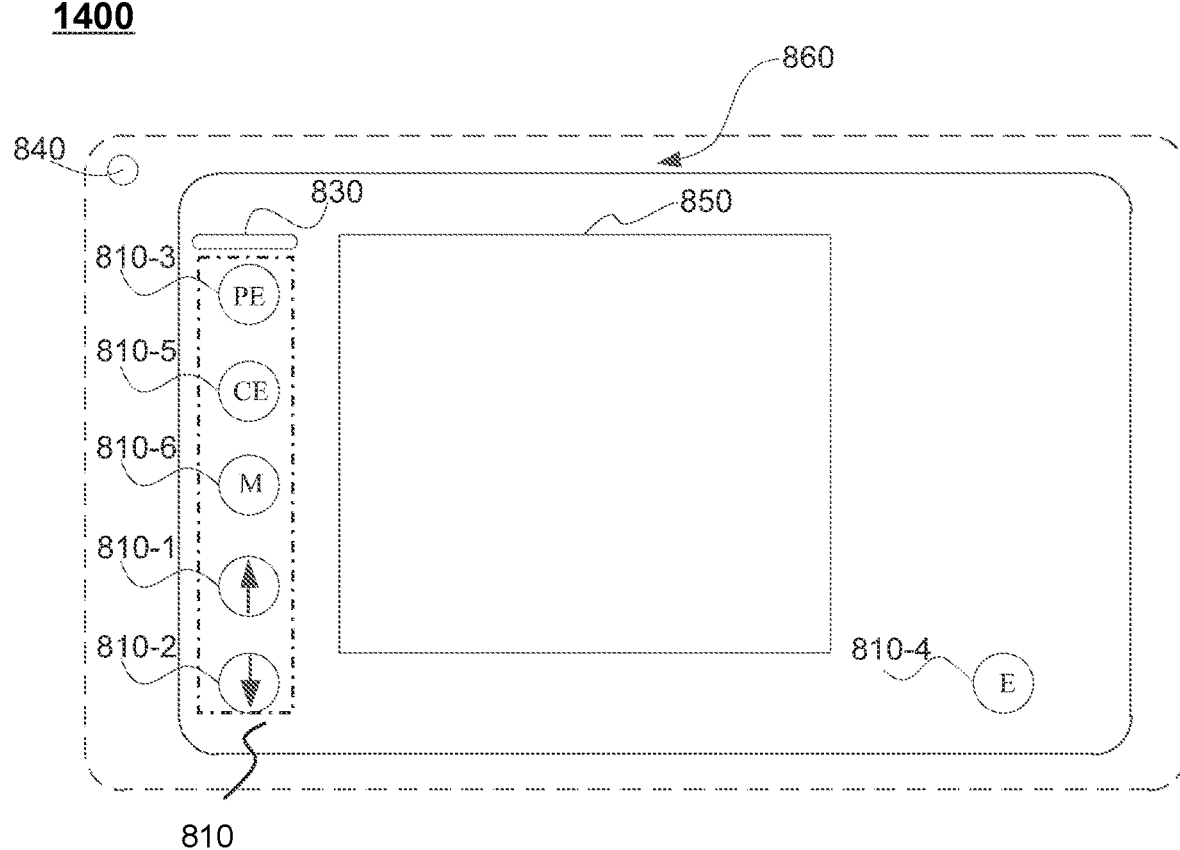
FIG. 14 is a schematic diagram illustrating an exemplary terminal according to some embodiments of the present disclosure.

FIG. 14 is a schematic diagram illustrating an exemplary terminal 1400 according to some embodiments of the present disclosure. The terminal 1400 may be similar to the terminal 800, except for certain components or features. For example, the terminal 1400 may not include the complementary key 820. The function keys 810 may further include a cancel key 810-5 and a movable key 810-6. The selection of the movable key 810-6 may cause the terminal 1400 to direct the X-ray imaging device 110 to operate in a movable state. A portion of the function keys 810 may be arranged in an array as illustrated in FIG. 14. In some embodiments, the function keys 810 may be physical keys.

In some embodiments, the selection of the function key 810 may cause the terminal 1400 to switch the operating state of the X-ray imaging device 110 only when the input received satisfies a switch condition (e.g., the time length of the function key 810 being selected exceeding a time threshold). More descriptions regarding the switch condition may be found elsewhere in the present disclosure (e.g., FIGS. 6 and 7 and the relevant descriptions thereof).

It should be noted that the examples illustrated in FIG. 9 to FIG. 14 are provided for the purposes of illustration, and not intended to limit the scope of the present disclosure. For persons having ordinary skills in the art, steps may be combined in various ways or switched with other steps. Various variations and modifications may be conducted after understanding the process. However, those variations and modifications may not depart from the spirit and scope of this disclosure. In some embodiments, the terminal 900, the terminal 1000, the terminal 1100, the terminal 1200, the terminal 1300, or the terminal 1400 may include one or more additional components not described, and/or without one or more of the components discussed. For example, the moving forward key 810-1 and/or the moving backward key 810-2 may be omitted. In some embodiments, the components (e.g., the function key 810, the complementary key 820, the status bar 830) may be arranged in any shape, size, and configuration.

Figure 15A:
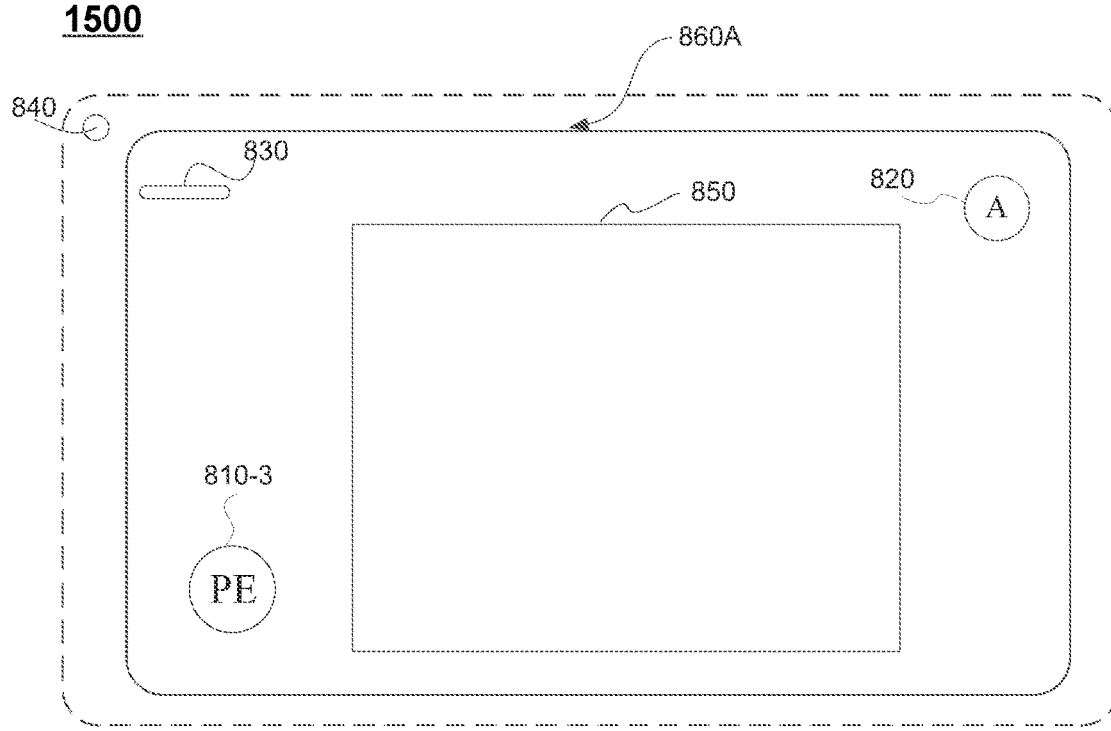
FIGS. 15A and 15B are schematic diagrams illustrating exemplary interfaces of a terminal according to some embodiments of the present disclosure.
Figure 15B:
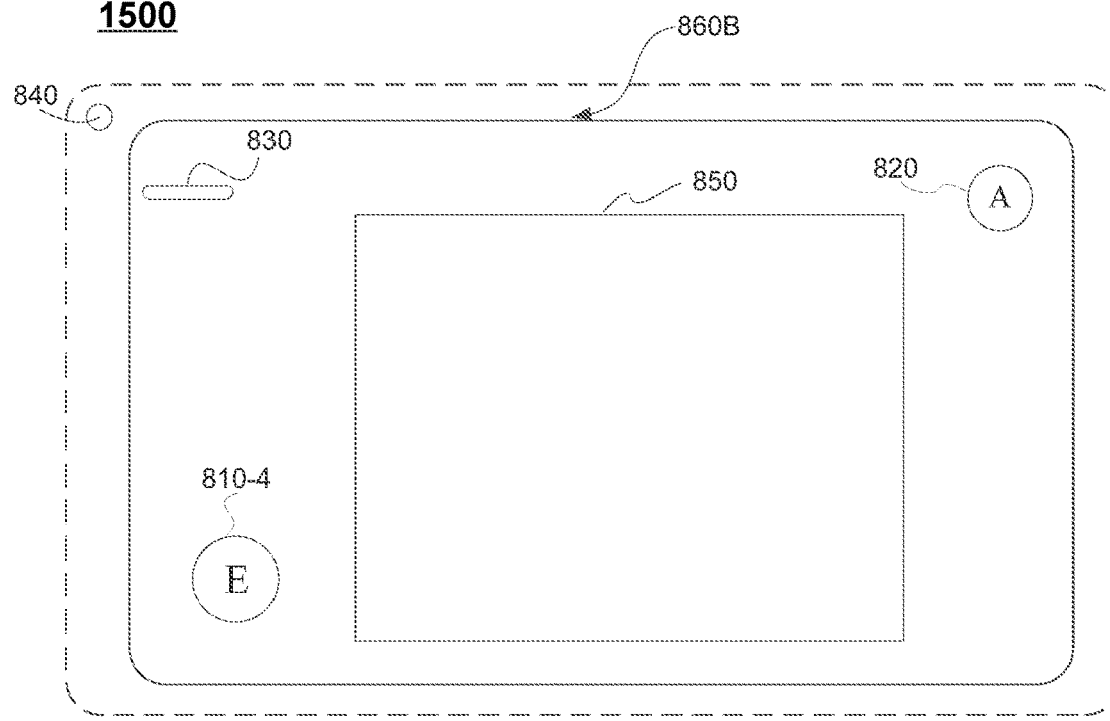

FIGS. 15A and 15B are schematic diagrams illustrating exemplary interfaces of a terminal 1500 according to some embodiments of the present disclosure. The terminal 1500 may be similar to the terminal 800, except for certain components or features. The interface of the terminal 1500 may be adjusted according to the operating state of the X-ray imaging device 110. For example, different function keys 810 may be displayed when the X-ray imaging device 110 operates in different operating states.

In some embodiments, when the X-ray imaging device 110 operates in the exposure pending state, the terminal 1500 may display an interface 860A as illustrated in FIG. 15A. The exposure preparation key 810-3 may be displayed in the interface 860A.

When the terminal 1500 receives an input to switch the X-ray imaging device 110 to the exposure preparation state and the input satisfies a certain condition (if any), the interface of the terminal 1500 may change to an interface 860B as illustrated in FIG. 15B. The exposure key 810-4 may be displayed in the interface 860B.

Figure 16A:
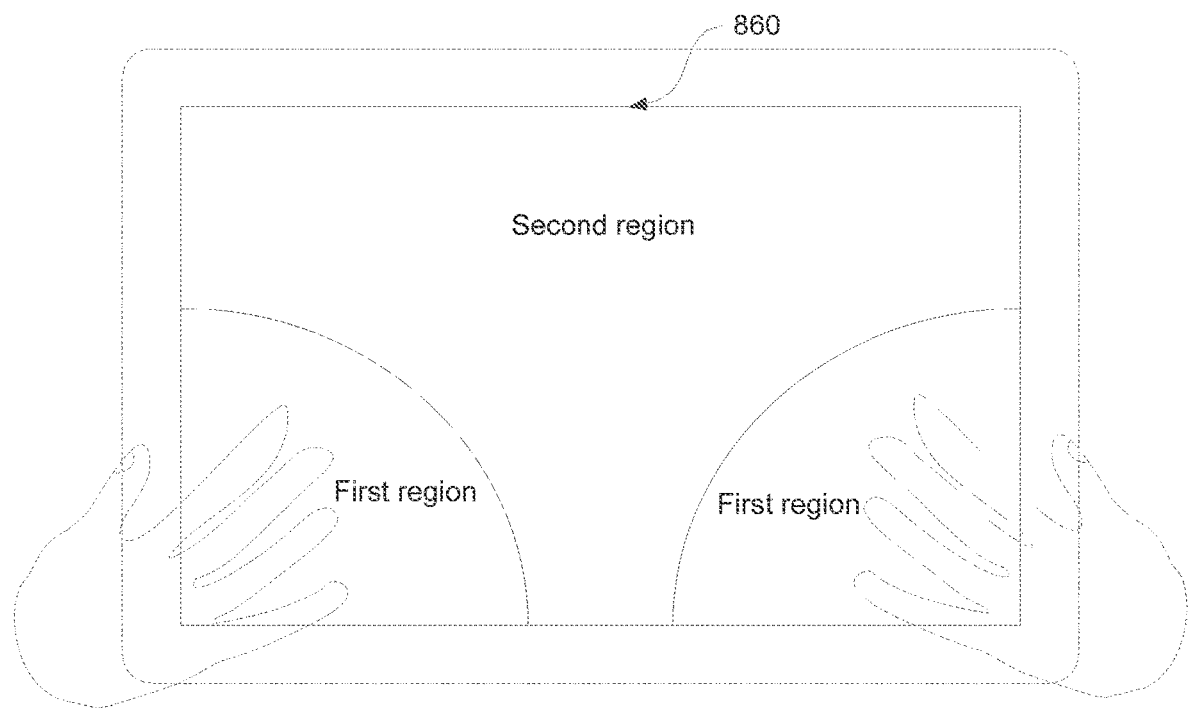
FIGS. 16A and 16B are schematic diagrams illustrating regions of an exemplary interface of a terminal according to some embodiments of the present disclosure.
Figure 16B:
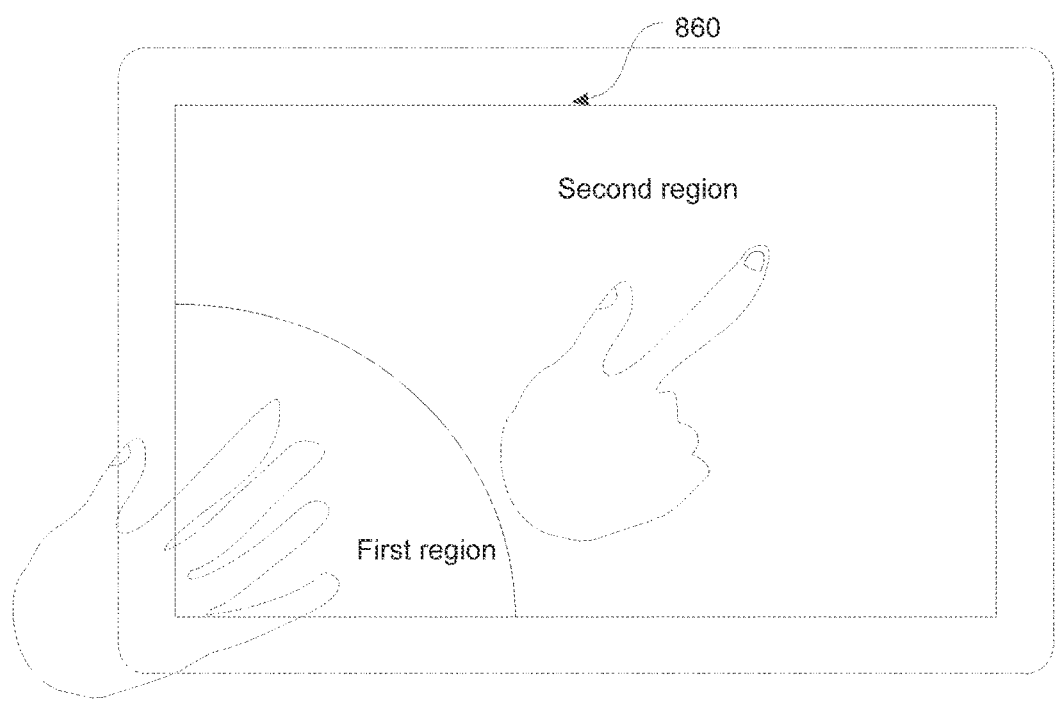

FIGS. 16A and 16B are schematic diagrams illustrating exemplary regions of an interface of a terminal according to some embodiments of the present disclosure. The first region may be a region where a user usually touches when he or she holds the terminal, and the second region may be a region where a user does not usually touch when he or she holds the terminal.

In some embodiments, as shown in FIG. 16A, the first region may include the bottom-left region and the bottom-right region of the interface 860. The second region may be the region on the interface 860 other than the first region. In some embodiments, as shown in FIG. 16B, the first region may be the bottom-left region of the interface 860. The second region may be the region on the interface 860 other than the first region.

In some embodiments, the function keys 810 may be located in the first region and the complementary key 820 may be located in the second region of the interface 860.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable medium having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
    at least one storage device storing a set of instructions for controlling an X-ray imaging device that operates in a first operating state; and
    at least one processor configured to communicate with the at least one storage device, wherein when executing the set of instructions, the at least one processor is configured to direct the system to perform operations including:
    causing a first interface to be displayed via a terminal, the first interface corresponding to a second operating state of the X-ray imaging device;
    obtaining, via the first interface of the terminal, a first input from a user, the first input being associated with the second operating state of the X-ray imaging device;
    in response to the first input, causing the X-ray imaging device to switch from the first operating state to the second operating state and causing a second interface to be displayed via the terminal, the second interface corresponding to a third operating state of the X-ray imaging device;
    determining whether a second input that satisfies a switch condition associated with the third operating state is received from the user via the second interface of the terminal, the second input being associated with the third operating state of the X-ray imaging device; and
    in response to determining that the second input that satisfies the switch condition associated with the third operating state is received from the user, causing the X-ray imaging device to switch from the second operating state to the third operating state; or in response to determining that the second input that satisfies the switch condition associated with the third operating state is not received from the user, causing the X-ray imaging device to switch from the second operating state back to the first operating state.

2. The system of claim 1, wherein the determining whether a second input that satisfies a switch condition associated with the third operating state is received from the user via the second interface of the terminal comprises:
    determining whether a second input associated with the third operating state is obtained within a preset period after the X-ray imaging device switches from the first operating state to the second operating state; and
    in response to determining that a second input associated with the third operating state is obtained within the preset period, determining that a second input that satisfies the switch condition associated with the third operating state is received from the user via the second interface of the terminal.

3. The system of claim 1, wherein the terminal includes a function key corresponding to the third operating state and a complementary key, and
    the determining whether a second input that satisfies a switch condition associated with the third operating state is received from the user via the second interface of the terminal comprises:
    determining whether the second input includes a first selection of the function key and a second selection of the complementary key; and
    in response to determining that the second input includes the first selection and the second selection, determining that a second input that satisfies the switch condition associated with the third operating state is received from the user via the second interface of the terminal.

4. The system of claim 3, wherein
    the terminal includes a user interface,
    the user interface includes a first region for the user to hold the terminal and a second region other than the first region,
    the function key is located in the first region, and
    the complementary key is located in the second region.

5. The system of claim 1, wherein the terminal includes an interface element, and the interface element changes its color when the X-ray imaging device switches to at least one of the second operating state or the third operating state.

6. The system of claim 5, wherein the interface element includes a status bar.

7. The system of claim 1, wherein the terminal includes an interface element for indicating a communication status between the terminal and the X-ray imaging device.

8. The system of claim 1, wherein in response to the first input, the causing the X-ray imaging device to switch from the first operating state to the second operating state comprises:
    determining whether the first input satisfies a switch condition associated with the second operating state; and
    in response to determining that the first input satisfies the switch condition associated with the second operating state, causing the X-ray imaging device to switch from the first operating state to the second operating state.

9. The system of claim 1, wherein
    the first operating state is an exposure pending state,
    the second operating state is an exposure preparation state, and
    the third operating state is an exposure state.

10. A method for controlling an X-ray imaging device that operates in a first operating state, the method being implemented on a computing device having at least one processor and at least one storage device, the method comprising:
    causing a first interface to be displayed via a terminal, the first interface corresponding to a second operating state of the X-ray imaging device;
    obtaining, via the first interface of the terminal, a first input from a user, the first input being associated with the second operating state of the X-ray imaging device;
    in response to the first input, causing the X-ray imaging device to switch from the first operating state to the second operating state and causing a second interface to be displayed via the terminal, the second interface corresponding to a third operating state of the X-ray imaging device;
    determining whether a second input that satisfies a switch condition associated with the third operating state is received from the user via the second interface of the terminal, the second input being associated with the third operating state of the X-ray imaging device; and
    in response to determining that the second input that satisfies the switch condition associated with the third operating state is received from the user, causing the X-ray imaging device to switch from the second operating state to the third operating state; or in response to determining that the second input that satisfies the switch condition associated with the third operating state is not received from the user, causing the X-ray imaging device to switch from the second operating state back to the first operating state.

11. The method of claim 10, wherein the determining whether a second input that satisfies a switch condition associated with the third operating state is received from the user via the second interface of the terminal comprises:
  determining whether a second input associated with the third operating state is obtained within a preset period after the X-ray imaging device switches from the first operating state to the second operating state; and
  in response to determining that a second input associated with the third operating state is obtained within the preset period, determining that a second input that satisfies the switch condition associated with the third operating state is received from the user via the second interface of the terminal.

12. The method of claim 10, wherein the terminal includes a function key corresponding to the third operating state and a complementary key, and
  the determining whether a second input that satisfies a switch condition associated with the third operating state is received from the user via the second interface of the terminal comprises:
  determining whether the second input includes a first selection of the function key and a second selection of the complementary key; and
  in response to determining that the second input includes the first selection and the second selection, determining that a second input that satisfies the switch condition associated with the third operating state is received from the user via the second interface of the terminal.

13. The method of claim 12, wherein
  the terminal includes a user interface,
  the user interface includes a first region for the user to hold the terminal and a second region other than the first region,
  the function key is located in the first region, and
  the complementary key is located in the second region.

14. The method of claim 10, wherein the terminal includes an interface element, and the interface element changes its color when the X-ray imaging device switches to at least one of the second operating state or the third operating state.

15. The method of claim 14, wherein the interface element includes a status bar.

16. The method of claim 10, wherein the terminal includes an interface element for indicating a communication status between the terminal and the X-ray imaging device.

17. The method of claim 10, wherein in response to the first input, the causing the X-ray imaging device to switch from the first operating state to the second operating state comprises:
  determining whether the first input satisfies a switch condition associated with the second operating state; and
  in response to determining that the first input satisfies the switch condition associated with the second operating state, causing the X-ray imaging device to switch from the first operating state to the second operating state.

18. A non-transitory computer readable medium, comprising a set of instructions for controlling an X-ray imaging device that operates in a first operating state, wherein when executed by at least one processor, the set of instructions direct the at least one processor to effectuate a method, the method comprising:
  causing a first interface to be displayed via a terminal, the first interface corresponding to a second operating state of the X-ray imaging device;
  obtaining, via the first interface of the terminal, a first input from a user, the first input being associated with the second operating state of the X-ray imaging device;
  in response to the first input, causing the X-ray imaging device to switch from the first operating state to the second operating state and causing a second interface to be displayed via the terminal, the second interface corresponding to a third operating state of the X-ray imaging device;
  determining whether a second input that satisfies a switch condition associated with the third operating state is received from the user via the second interface of the terminal, the second input being associated with the third operating state of the X-ray imaging device; and
  in response to determining that the second input that satisfies the switch condition associated with the third operating state is received from the user, causing the X-ray imaging device to switch from the second operating state to the third operating state; or
  in response to determining that the second input that satisfies the switch condition associated with the third operating state is not received from the user, causing the X-ray imaging device to switch from the second operating state back to the first operating state.

19. The non-transitory computer readable medium of claim 18, wherein the determining whether a second input that satisfies a switch condition associated with the third operating state is received from the user via the second interface of the terminal comprises:
  determining whether a second input associated with the third operating state is obtained within a preset period after the X-ray imaging device switches from the first operating state to the second operating state; and
  in response to determining that the second input associated with the third operating state is obtained within the preset period, determining that a second input that satisfies the switch condition associated with the third operating state is received from the user via the second interface of the terminal.

20. The non-transitory computer readable medium of claim 18, wherein the terminal includes a function key corresponding to the third operating state and a complementary key, and
  the determining whether a second input that satisfies a switch condition associated with the third operating state is received from the user via the second interface of the terminal comprises:
  determining whether the second input includes a first selection of the function key and a second selection of the complementary key; and
  in response to determining that the second input includes the first selection and the second selection, determining that a second input that satisfies the switch condition associated with the third operating state is received from the user via the second interface of the terminal.

* * * * *